United States Patent
Li

(10) Patent No.: US 10,056,567 B2
(45) Date of Patent: Aug. 21, 2018

(54) CHIRAL METAL COMPLEXES AS EMITTERS FOR ORGANIC POLARIZED ELECTROLUMINESCENT DEVICES

(71) Applicant: ARIZONA BOARD OF REGENTS ON BEHALF OF ARIZONA STATE UNIVERSITY, Scottsdale, AZ (US)

(72) Inventor: Jian Li, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 15/119,961

(22) PCT Filed: Feb. 27, 2015

(86) PCT No.: PCT/US2015/018195
§ 371 (c)(1),
(2) Date: Aug. 18, 2016

(87) PCT Pub. No.: WO2015/131158
PCT Pub. Date: Sep. 3, 2015

(65) Prior Publication Data
US 2017/0069855 A1    Mar. 9, 2017

Related U.S. Application Data

(60) Provisional application No. 61/945,940, filed on Feb. 28, 2014.

(51) Int. Cl.
*C07F 15/00* (2006.01)
*H01L 51/00* (2006.01)
(Continued)

(52) U.S. Cl.
CPC ...... *H01L 51/0085* (2013.01); *C07F 15/0033* (2013.01); *C07F 15/0086* (2013.01);
(Continued)

(58) Field of Classification Search
CPC ....................................................... C07F 15/00
(Continued)

(56) References Cited

U.S. PATENT DOCUMENTS 4,769,292 A  9/1988 Tang et al.
5,707,745 A  1/1998 Forrest et al.
(Continued)

FOREIGN PATENT DOCUMENTS

CN  1680366 A  10/2005
CN  1777663     5/2006
(Continued)

OTHER PUBLICATIONS

Chew, S. et al.: Photoluminescence and electroluminescence of a new blue-emitting homoleptic iridium complex. Applied Phys. letters; vol. 88, pp. 093510-1-093510-3, 2006.*
(Continued)

*Primary Examiner* — Charanjit Aulakh
(74) *Attorney, Agent, or Firm* — Fish & Richardson P.C.

(57) ABSTRACT

Chiral metal complexes having one of general formulae (1)-(4).

(Continued)

-continued (4)

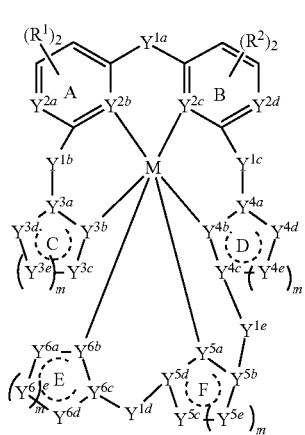

1 Claim, 16 Drawing Sheets

(51) Int. Cl.
C09K 11/06 (2006.01)
H01L 51/50 (2006.01)

(52) U.S. Cl.
CPC ............ *C09K 11/06* (2013.01); *H01L 51/009* (2013.01); *H01L 51/0087* (2013.01); *C09K 2211/1007* (2013.01); *C09K 2211/1029* (2013.01); *C09K 2211/1044* (2013.01); *C09K 2211/185* (2013.01); *H01L 51/5016* (2013.01); *H01L 51/5056* (2013.01); *H01L 51/5072* (2013.01)

(58) Field of Classification Search
USPC ...................................................... 546/10, 2
See application file for complete search history.

(56) References Cited

U.S. PATENT DOCUMENTS

| | | | |
|---|---|---|---|
| 5,844,363 A | 12/1998 | Gu et al. |
| 6,200,695 B1 | 3/2001 | Arai et al. |
| 6,303,238 B1 | 10/2001 | Thompson et al. |
| 6,780,528 B2 | 8/2004 | Tsuboyama et al. |
| 7,002,013 B1 | 2/2006 | Chi et al. |
| 7,026,480 B2 | 4/2006 | Che et al. |
| 7,029,766 B2 | 4/2006 | Huo et al. |
| 7,037,599 B2 | 5/2006 | Culligan et al. |
| 7,166,368 B2 | 1/2007 | Lecloux et al. |
| 7,276,617 B2 | 10/2007 | Sotoyama |
| 7,279,704 B2 | 10/2007 | Walters et al. |
| 7,332,232 B2 | 2/2008 | Ma et al. |
| 7,442,797 B2 | 10/2008 | Itoh et al. |
| 7,501,190 B2 | 3/2009 | Ise |
| 7,655,322 B2 | 2/2010 | Forrest et al. |
| 7,947,383 B2 | 5/2011 | Ise et al. |
| 8,133,597 B2 | 3/2012 | Yasukawa et al. |
| 8,389,725 B2 | 3/2013 | Li et al. |
| 8,617,723 B2 | 12/2013 | Stoessel |
| 8,816,080 B2 | 8/2014 | Li et al. |
| 8,871,361 B2 | 10/2014 | Xia et al. |
| 8,927,713 B2 | 1/2015 | Li et al. |
| 8,946,417 B2 | 2/2015 | Li et al. |
| 9,059,412 B2 | 6/2015 | Zeng et al. |
| 9,224,963 B2 | 12/2015 | Li et al. |
| 9,238,668 B2 | 1/2016 | Li et al. |
| 9,312,502 B2 | 4/2016 | Li et al. |
| 9,312,505 B2 | 4/2016 | Brooks et al. |
| 9,324,957 B2 | 4/2016 | Li et al. |
| 9,382,273 B2 | 7/2016 | Li |
| 9,385,329 B2 | 7/2016 | Li et al. |
| 9,425,415 B2 | 8/2016 | Li et al. |
| 9,461,254 B2 | 10/2016 | Tsai et al. |
| 9,550,801 B2 | 1/2017 | Li et al. |
| 9,617,291 B2 | 4/2017 | Li et al. |
| 9,673,409 B2 | 6/2017 | Li et al. |
| 9,698,359 B2 | 7/2017 | Li et al. |
| 9,711,739 B2 | 7/2017 | Li |
| 9,711,742 B2 | 7/2017 | Li et al. |
| 9,755,163 B2 | 9/2017 | Li et al. |
| 9,818,959 B2 | 11/2017 | Li |
| 9,865,825 B2 | 1/2018 | Li et al. |
| 9,879,039 B2 | 1/2018 | Li |
| 9,882,150 B2 | 1/2018 | Li |
| 2002/0068190 A1 | 6/2002 | Tsuboyama et al. |
| 2002/0189666 A1 | 12/2002 | Forrest et al. |
| 2003/0062519 A1 | 4/2003 | Yamazaki et al. |
| 2003/0186077 A1 | 10/2003 | Chen |
| 2004/0230061 A1 | 11/2004 | Seo et al. |
| 2005/0170207 A1 | 8/2005 | Ma et al. |
| 2005/0260446 A1 | 11/2005 | Mackenzie et al. |
| 2006/0073359 A1 | 4/2006 | Ise et al. |
| 2006/0093854 A1 | 5/2006 | Sotoyama et al. |
| 2006/0094875 A1 | 5/2006 | Itoh et al. |
| 2006/0127696 A1 | 6/2006 | Stossel et al. |
| 2006/0182992 A1 | 8/2006 | Nii et al. |
| 2006/0202197 A1 | 9/2006 | Nakayama et al. |
| 2006/0210831 A1 | 9/2006 | Sano et al. |
| 2006/0263635 A1 | 11/2006 | Ise |
| 2006/0286406 A1 | 12/2006 | Igarashi et al. |
| 2007/0057630 A1 | 3/2007 | Nishita et al. |
| 2007/0059551 A1 | 3/2007 | Yamazaki |
| 2007/0082284 A1 | 4/2007 | Stoessel et al. |
| 2007/0103060 A1 | 5/2007 | Itoh et al. |
| 2007/0111025 A1 | 5/2007 | Lennartz et al. |
| 2007/0224447 A1 | 9/2007 | Sotoyama et al. |
| 2008/0001530 A1 | 1/2008 | Ise et al. |
| 2008/0036373 A1 | 2/2008 | Itoh et al. |
| 2008/0054799 A1 | 3/2008 | Satou |
| 2008/0067925 A1 | 3/2008 | Oshiyama et al. |
| 2008/0079358 A1 | 4/2008 | Satou |
| 2008/0111476 A1 | 5/2008 | Choi et al. |
| 2008/0241518 A1 | 10/2008 | Satou et al. |
| 2008/0241589 A1 | 10/2008 | Fukunaga et al. |
| 2008/0269491 A1 | 10/2008 | Jabbour et al. |
| 2009/0026936 A1 | 1/2009 | Satou et al. |
| 2009/0026939 A1 | 1/2009 | Kinoshita et al. |
| 2009/0032989 A1 | 2/2009 | Karim et al. |
| 2009/0039768 A1 | 2/2009 | Igarashi et al. |
| 2009/0079340 A1 | 3/2009 | Kinoshita et al. |
| 2009/0128008 A1 | 5/2009 | Ise et al. |
| 2009/0218561 A1 | 9/2009 | Kitamura et al. |
| 2009/0261721 A1 | 10/2009 | Murakami et al. |
| 2009/0267500 A1 | 10/2009 | Kinoshita et al. |
| 2010/0000606 A1 | 1/2010 | Thompson et al. |
| 2010/0013386 A1 | 1/2010 | Thompson et al. |
| 2010/0171111 A1 | 7/2010 | Takada et al. |
| 2010/0270540 A1 | 10/2010 | Chung et al. |
| 2011/0049496 A1 | 3/2011 | Fukuzaki |
| 2012/0095232 A1 | 4/2012 | Li et al. |
| 2012/0181528 A1 | 7/2012 | Takada et al. |
| 2012/0215001 A1 | 8/2012 | Li et al. |
| 2012/0223634 A1 | 9/2012 | Xia et al. |
| 2012/0273736 A1 | 11/2012 | James et al. |
| 2012/0302753 A1 | 11/2012 | Li |
| 2013/0048963 A1 | 2/2013 | Beers et al. |
| 2013/0168656 A1 | 7/2013 | Tsai et al. |
| 2013/0203996 A1 | 8/2013 | Li et al. |
| 2013/0237706 A1 | 9/2013 | Li |
| 2013/0341600 A1 | 12/2013 | Lin et al. |
| 2014/0014922 A1 | 1/2014 | Lin et al. |
| 2014/0027733 A1 | 1/2014 | Zeng et al. |
| 2014/0084261 A1 | 3/2014 | Brooks et al. |
| 2014/0114072 A1 | 4/2014 | Li et al. |
| 2014/0191206 A1 | 7/2014 | Cho |
| 2014/0203248 A1 | 7/2014 | Zhou et al. |
| 2014/0326960 A1 | 11/2014 | Kim et al. |

(56) References Cited

U.S. PATENT DOCUMENTS

| | | |
|---|---|---|
| 2014/0330019 A1 | 11/2014 | Li et al. |
| 2014/0364605 A1 | 12/2014 | Li et al. |
| 2015/0008419 A1 | 1/2015 | Li |
| 2015/0028323 A1 | 1/2015 | Xia et al. |
| 2015/0069334 A1 | 3/2015 | Xia et al. |
| 2015/0105556 A1 | 4/2015 | Li et al. |
| 2015/0162552 A1 | 6/2015 | Li et al. |
| 2015/0194616 A1 | 7/2015 | Li et al. |
| 2015/0228914 A1 | 8/2015 | Li et al. |
| 2015/0287938 A1 | 10/2015 | Li et al. |
| 2015/0318500 A1 | 11/2015 | Li |
| 2015/0349279 A1 | 12/2015 | Li et al. |
| 2015/0380666 A1 | 12/2015 | Szigethy |
| 2016/0028028 A1 | 1/2016 | Li et al. |
| 2016/0043331 A1 | 2/2016 | Li et al. |
| 2016/0072082 A1 | 3/2016 | Brooks et al. |
| 2016/0133861 A1 | 5/2016 | Li |
| 2016/0133862 A1 | 5/2016 | Li et al. |
| 2016/0197291 A1 | 7/2016 | Xia et al. |
| 2016/0285015 A1 | 9/2016 | Li et al. |
| 2016/0359120 A1 | 12/2016 | Li |
| 2016/0359125 A1 | 12/2016 | Li et al. |
| 2017/0005278 A1 | 1/2017 | Li et al. |
| 2017/0012224 A1 | 1/2017 | Li et al. |
| 2017/0047533 A1 | 2/2017 | Li et al. |
| 2017/0066792 A1 | 3/2017 | Li et al. |
| 2017/0267923 A1 | 9/2017 | Li |
| 2018/0006246 A1 | 1/2018 | Li |

FOREIGN PATENT DOCUMENTS

| | | |
|---|---|---|
| CN | 1894269 | 1/2007 |
| CN | 101142223 | 3/2008 |
| CN | 101667626 | 3/2010 |
| CN | 102449108 A | 5/2012 |
| CN | 102892860 | 1/2013 |
| CN | 102971396 | 3/2013 |
| CN | 104232076 | 12/2014 |
| CN | 104693243 | 6/2015 |
| CN | 105367605 | 3/2016 |
| CN | 105418591 | 3/2016 |
| EP | 1808052 | 7/2007 |
| EP | 1874893 | 1/2008 |
| EP | 1874894 | 1/2008 |
| EP | 1919928 | 5/2008 |
| EP | 2036907 | 3/2009 |
| EP | 2096690 A2 | 9/2009 |
| EP | 2417217 | 2/2012 |
| EP | 2112213 | 7/2012 |
| EP | 2711999 | 3/2014 |
| JP | 2005267557 | 9/2005 |
| JP | 2005310733 | 11/2005 |
| JP | 2006047240 | 2/2006 |
| JP | 2006114889 | 4/2006 |
| JP | 2006232784 | 9/2006 |
| JP | 2006242080 | 9/2006 |
| JP | 2006242081 | 9/2006 |
| JP | 2006256999 | 9/2006 |
| JP | 2006257238 | 9/2006 |
| JP | 2006261623 | 9/2006 |
| JP | 2006282965 | 10/2006 |
| JP | 2006290988 | 10/2006 |
| JP | 2006313796 | 11/2006 |
| JP | 2006332622 | 12/2006 |
| JP | 2006351638 | 12/2006 |
| JP | 2007019462 | 1/2007 |
| JP | 2007031678 A | 2/2007 |
| JP | 2007042875 | 2/2007 |
| JP | 2007053132 | 3/2007 |
| JP | 2007066581 | 3/2007 |
| JP | 2007073620 | 3/2007 |
| JP | 2007073845 | 3/2007 |
| JP | 2007073900 | 3/2007 |
| JP | 2007080593 | 3/2007 |
| JP | 2007080677 | 3/2007 |
| JP | 2007088105 | 4/2007 |
| JP | 2007088164 | 4/2007 |
| JP | 2007096259 | 4/2007 |
| JP | 2007110067 | 4/2007 |
| JP | 2007110102 | 4/2007 |
| JP | 2007258550 | 10/2007 |
| JP | 2007324309 | 12/2007 |
| JP | 2008010353 | 1/2008 |
| JP | 2008091860 | 4/2008 |
| JP | 2008103535 | 5/2008 |
| JP | 2008108617 | 5/2008 |
| JP | 2008109085 | 5/2008 |
| JP | 2008109103 | 5/2008 |
| JP | 2008160087 | 7/2008 |
| JP | 2008198801 | 8/2008 |
| JP | 2008270729 | 11/2008 |
| JP | 2008270736 | 11/2008 |
| JP | 2009016184 | 1/2009 |
| JP | 2009016579 | 1/2009 |
| JP | 2009032977 | 2/2009 |
| JP | 2009032988 | 2/2009 |
| JP | 2009266943 | 11/2009 |
| JP | 2009267171 | 11/2009 |
| JP | 2009267244 | 11/2009 |
| JP | 2009272339 | 11/2009 |
| JP | 2009283891 | 12/2009 |
| JP | 2010135689 | 6/2010 |
| JP | 2012222255 | 11/2012 |
| JP | 2013525436 | 6/2013 |
| JP | 5604505 | 10/2014 |
| JP | 2014221807 | 11/2014 |
| JP | 2015081257 | 4/2015 |
| KR | 1020060115371 | 11/2006 |
| KR | 2007061830 | 6/2007 |
| KR | 2007112465 | 11/2007 |
| KR | 1020130043460 | 4/2013 |
| TW | 200701835 | 1/2007 |
| TW | 201307365 | 2/2013 |
| TW | 201710277 A1 | 3/2017 |
| WO | WO200070655 | 11/2000 |
| WO | WO2004003108 | 1/2004 |
| WO | WO2004039781 | 5/2004 |
| WO | WO2004108857 | 12/2004 |
| WO | WO2005042444 | 5/2005 |
| WO | WO2005042550 | 5/2005 |
| WO | WO2005075600 | 8/2005 |
| WO | WO2005103195 | 11/2005 |
| WO | WO2005105746 | 11/2005 |
| WO | WO2005113704 | 12/2005 |
| WO | WO2006033440 | 3/2006 |
| WO | WO2006067074 | 6/2006 |
| WO | WO2006/082742 | 8/2006 |
| WO | WO2006098505 | 9/2006 |
| WO | WO2006100888 | 9/2006 |
| WO | WO2006115299 | 11/2006 |
| WO | WO2006115301 | 11/2006 |
| WO | WO2007034985 | 3/2007 |
| WO | WO2007069498 | 6/2007 |
| WO | WO2008066192 | 6/2008 |
| WO | WO2008066195 | 6/2008 |
| WO | WO2008066196 | 6/2008 |
| WO | WO2008101842 | 8/2008 |
| WO | WO2008117889 | 10/2008 |
| WO | WO2008123540 | 10/2008 |
| WO | WO2009017211 | 2/2009 |
| WO | WO2009086209 | 7/2009 |
| WO | WO2009111299 | 9/2009 |
| WO | WO2010008098 | 1/2010 |
| WO | WO2010056669 | 5/2010 |
| WO | WO2010093176 | 8/2010 |
| WO | WO2010118026 | 10/2010 |
| WO | WO2011064335 | 6/2011 |
| WO | WO2011070989 | 6/2011 |
| WO | WO2011137429 | 11/2011 |
| WO | WO2011137431 | 11/2011 |
| WO | WO2012112853 | 8/2012 |
| WO | WO2012142387 | 10/2012 |
| WO | WO2012162488 | 11/2012 |
| WO | WO2012163471 | 12/2012 |

(56) References Cited

FOREIGN PATENT DOCUMENTS

| WO | WO2013130483 | 9/2013 |
|---|---|---|
| WO | WO2014016611 | 1/2014 |
| WO | WO2014031977 | 2/2014 |
| WO | WO2014047616 | 3/2014 |
| WO | WO2014109814 | 7/2014 |
| WO | WO2014208271 | 12/2014 |
| WO | WO2015027060 | 2/2015 |
| WO | WO2015131158 | 9/2015 |
| WO | WO2016025921 | 2/2016 |
| WO | WO2016029186 | 2/2016 |
| WO | WO2016197019 | 12/2016 |

OTHER PUBLICATIONS

International Search Report and Written Opinion mailed by the International Searching Authority dated May 14, 2015 for PCT/US2015/018195 filed Feb. 27, 2015 (pp. 1-17).
International Preliminary Report on Patentability mailed by the International Bureau dated Sep. 15, 2016 for PCT/US2015/018195 (pp. 1-12).
Wong; Challenges in organometallic research—Great opportunity for solar cells and OLEDs, Journal of Organometallic Chemistry, 2009, 694, 2644-2647.
JP2009267244, English Translation from EPO, Nov. 2009, 80 pages.
JP2010135689, English translation from EPO, Jun. 2010, 95 pages.
Chi et al.; Transition-metal phosphors with cyclometalating ligands: fundamentals and applications, Chemical Society Reviews, vol. 39, No. 2, Feb. 2010, pp. 638-655.
Satake et al., "Interconvertible Cationic and Neutral Pyridinylimidazole η3-Allylpalladium Complexes. Structural Assignment by 1H, 13C, and 15N NMR and X-ray Diffraction", Organometallics, vol. 18, No. 24, 1999, pp. 5108-5111.
Baldo et al., "Highly Efficient Phosphorescent Emission from Organic Electroluminescent Devices," Nature, vol. 395, Sep. 10, 1998, pp. 151-154.
Baldo et al., "Very high-efficiency green organic light-emitting devices based on electrophosphorescence," Applied Physics Letters, vol. 75, No. 1, Jul. 5, 1999, pp. 4-6.
Ying Yang et al., "Induction of Circularly Polarized Electroluminescence from an Achiral Light-Emitting Polymer via a Chiral Small-Molecule Dopant," Advanced Materials, vol. 25, Issue 18, May 14, 2013, pp. 2624-2628.
Ayan Maity et al., "Room-temperature synthesis of cyclometalated iridium(III) complexes; kinetic isomers and reactive functionalities" Chem. Sci., vol. 4, pp. 1175-1181 (2013).
Shiro Koseki et al., "Spin-orbit coupling analyses of the geometrical effects on phosphorescence in Ir(ppy)3 and its derivatives", J. Phys. Chem. C, vol. 117, pp. 5314-5327 (2013).
Ji Hyun Seo et al., "Efficient blue-green organic light-emitting diodes based on heteroleptic tris-cyclometalated iridium (III) complexes". Thin Solid Films, vol. 517, pp. 1807-1810 (2009).
Barry O'Brien et al.: White organic light emitting diodes using Pt-based red, green and blue phosphorescent dopants. Proc. SPIE, vol. 8829, pp. 1-6, Aug. 25, 2013.
Xiao-Chu Hang et al., "Highly Efficient Blue-Emitting Cyclometalated Platinum(II) Complexes by Judicious Molecular Design," Angewandte Chemie, International Edition, vol. 52, Issue 26, Jun. 24, 2013, pp. 6753-6756.
Vanessa Wood et al., "Colloidal quantum dot light-emitting devices," Nano Reviews, vol. 1, 2010, 8 pages.
Glauco Ponterini et al., "Comparison of Radiationless Decay Processes in Osmium and Platinum Porphyrins," J. Am. Chem. Soc., vol. 105, No. 14, 1983, pp. 4639-4645.
Shizuo Tokito et al., "Confinement of triplet energy on phosphorescent molecules for highly-efficient organic blue-light-emitting devices," Applied Physics Letters, vol. 83, No. 3, Jul. 21, 2003, pp. 569-571.

Brian W. D'Andrade et al., "Controlling Exciton Diffusion in Multilayer White Phosphorescent Organic Light Emitting Devices," Adv. Mater., vol. 14, No. 2, Jan. 16, 2002, pp. 147-151.
Dileep A. K. Vezzu et al., "Highly Luminescent Tetradentate Bis-Cyclometalated Platinum Complexes: Design, Synthesis, Structure, Photophysics, and Electroluminescence Application," Inorg. Chem., vol. 49, 2010, pp. 5107-5119.
Evan L. Williams et al., "Excimer-Based White Phosphorescent Organic Light Emitting Diodes with Nearly 100% Internal Quantum Efficiency," Adv. Mater., vol. 19, 2007, pp. 197-202.
Shih-Chun Lo et al., "High-Triplet-Energy Dendrons: Enhancing the Luminescence of Deep Blue Phosphorescent Iridium(III) Complexes," J. Am. Chem. Soc., vol. 131, 2009, pp. 16681-16688.
Jan Kalinowski et al., "Light-emitting devices based on organometallic platinum complexes as emitters," Coordination Chemistry Reviews, vol. 255, 2011, pp. 2401-2425.
Ke Feng et al., "Norbornene-Based Copolymers Containing Platinum Complexes and Bis(carbazolyl)benzene Groups in Their Side-Chains," Macromolecules, vol. 42, 2009, pp. 6855-6864.
Chi-Ming Che et al., "Photophysical Properties and OLED Applications of Phosphorescent Platinum(II) Schiff Base Complexes," Chem. Eur. J., vol. 16, 2010, pp. 233-247.
Stephen R. Forrest, "The path to ubiquitous and low-cost organic electronic appliances on plastic," Nature, vol. 428, Apr. 29, 2004, pp. 911-918.
Nicholas R. Evans et al., "Triplet Energy Back Transfer in Conjugated Polymers with Pendant Phosphorescent Iridium Complexes," J. Am. Chem. Soc., vol. 128, 2006, pp. 6647-6656.
Xiaofan Ren et al., "Ultrahigh Energy Gap Hosts in Deep Blue Organic Electrophosphorescent Devices," Chem. Mater., vol. 16, 2004, pp. 4743-4747.
Jeonghun Kwak et al., "Bright and Efficient Full-Color Colloidal Quantum Dot Light-Emitting Diodes Using an Inverted Device Structure," Nano Lett., 2012, Vo. 12, pp. 2362-2366.
Hirohiko Fukagawa et al., "Highly Efficient and Stable Red Phosphorescent Organic Light-Emitting Diodes Using Platinum Complexes," Adv. Mater., 2012, vol. 24, pp. 5099-5103.
Eric Turner et al., "Cyclometalated Platinum Complexes with Luminescent Quantum Yields Approaching 100%," Inorg. Chem., 2013, vol. 52, pp. 7344-7351.
Steven C. F. Kui et al., "Robust Phosphorescent Platinum(II) Complexes Containing Tetradentate ONCN Ligands: Excimeric Excited State and Application in Organic White-Light-Emitting Diodes," Chem. Eur. J., 2013, vol. 19, pp. 69-73.
Steven C. F. Kui et al., "Robust phosphorescent platinum(II) complexes with tetradentate ONCN ligands: high efficiency OLEDs with excellent efficiency stability," Chem. Commun., 2013, vol. 49, pp. 1497-1499.
Guijie Li et al., "Efficient and stable red organic light emitting devices from a tetradentate cyclometalated platinum complex," Organic Electronics, 2014, vol. 15 pp. 1862-1867.
Guijie Li et al., Efficient and Stable White Organic Light-Emitting Diodes Employing a Single Emitter, Adv. Mater., 2014, vol. 26, pp. 2931-2936.
Barry O'Brien et al., "High efficiency white organic light emitting diodes employing blue and red platinum emitters," Journal of Photonics for Energy, vol. 4, 2014, pp. 043597-1-8.
Kai Li et al., "Light-emitting platinum(II) complexes supported by tetradentate dianionic bis(N-heterocyclic carbene) ligands: towards robust blue electrophosphors," Chem. Sci., 2013, vol. 4, pp. 2630-2644.
Tyler Fleetham et al., "Efficient "pure" blue OLEDs employing tetradentate Pt complexes with a narrow spectral bandwidth," Advanced Materials (Weinheim, Germany), Vo. 26, No. 41, 2014, pp. 7116-7121.
Dorwald; "Side Reactions in Organic Synthesis: A Guide to Successful Synthesis Design," Chapter 1, 2005 Wiley-VCH Verlag GmbH & Co. KGaA, Weinheim, 32 pages.
Murakami; JP 2007258550, English machine translation from EPO, Oct. 4, 2007. 80 pages.
Murakami; JP 2007324309, English machine translation from EPO, Dec. 13, 2007, 89 pages.

(56) References Cited

OTHER PUBLICATIONS

Marc Lepeltier et al., "Efficient blue green organic light-emitting devices based on a monofluorinated heteroleptic iridium(III) complex," Synthetic Metals, vol. 199, 2015, pp. 139-146.
Stefan Bernhard, "The First Six Years: A Report," Department of Chemistry, Princeton University, May 2008, 11 pages.
S. A. Willison et al., "A Luminscent Platinum(II) 2,6-Bis(N-pyrazolyl)pyridine Complex", Inorg. Chem. vol. 43, pp. 2548-2555, 2004.
J. M. Longmire et al., "Synthesis and X-ray Crystal Structures of Palladium(II) and Platinum(II) Complexes of the PCP-Type Chiral Tridenate Ligand", Organometallics, vol. 17, pp. 4374-4379, 1998.
V. Adamovich et al., "High efficiency single dopant white electrophosphorescent light emitting diodes", New J. Chem, vol. 26, pp. 1171-1178. 2002.
Del Cano et al., "Near-infrared electroluminescence based on perylenediimide-doped tris(8-quinolinolato) aluminum", Applied Physics Letters, 88, pp. 071117-1-071117-3, 2006.
B. Harrison et al., "Near-infrared electroluminescence from conjugated polymer/lanthanide porphyrin blends", Applied Physics Letter, vol. 79, No. 23, pp. 3770-3772, Dec. 3, 2001.
J. Kido et al., "Organo Lanthanide Metal Complexes for Electroluminscent Materials", Chem. Rev., vol. 102, pp. 2357-2368, 2002.
S. Lamansky et al., "Highly Phosphorescent Bis-Cyclometalated Iridium Complexes: Synthesis, Photophysical Characterization, and Use in Organic Light Emitting Diodes", J. Am. Chem. Soc., vol. 123, pp. 4304-4312, 2001.
S. Lamansky et al., "Synthesis and Characterization of Phosphorescent Cyclometalated Iridium Complexes", Inorg. Chem., vol. 40, pp. 1704-1711, 2001.
X. Li et al., "Synthesis and properties of novel poly(p-phenylenevinylene) copolymers for near-infrared emitting diodes", European Polymer Journal, vol. 41, pp. 2923-2933, 2005.
P. Peumans et al., "Small molecular weight organic thin-film photodetectors and solar cells", Journal of Applied Physics, vol. 93, No. 7, pp. 3693-3723, Apr. 1, 2003.
Rand et al., Organic Double-Heterostructure Photovoltaic Cells Employing Thick Tris (acetylacetonato) ruthenium (III) Exciton-Blocking Layers, Advanced Materials vol. 17, pp. 2714-2718, 2005.
C.W. Tang "Two-layer organic photovoltaic cell", Appl. Phys. Letters 48 (2), pp. 183-185, 1986).
Vanhelmont et al., "Synthesis, Crystal Structure, High-Resolution Optical Spectroscopy, and Extended Huckel Calculations for [Re(CO)4(thpy)] (thpy-2(2-Thienyl)pyridinate). Comparison with Related Cyclometalated Complexes", Inorg. Chem., vol. 36, pp. 5512-5517, 1997.
Williams et al., "Organic light-emitting diodes having exclusive near-infrared electrophospherescence", Applied Physics Letters, vol. 89, pp. 083506 (3 pages), 2006.
Forrest et al., "Measuring the Efficiency of Organic Light-Emitting Devices", Advanced Materials, vol. 15, No. 13, pp. 1043-1048, 2003.
Cardenas et al., "Divergent Behavior of Palladium(II) and Platinum(II) in the Metalation of 1,2-Di(2-pyridyl)benzene," Organometallics 1999, 18, pp. 3337-3341.
Williams et al., "An Alternative Route to Highly Luminescent Platinum(II) Complexes," Inorg. Chem., 2003, 42, pp. 8609-8611.
Sanna et al., "Platinum complexes with N—N—C ligands. Synthesis, electrochemical and spectroscopic characteristics of platinum(II) and relevant electroreduced species," Inorganica Chimica Acta 305, 2000, pp. 189-205.
International Search Report and Written Opinion, PCT/US2008/087847, dated Aug. 6, 2009, 12 pages.
International Search Report and Written Opinion, PCT/US2009/035441, dated Oct. 19, 2009, 14 pages.
Ionkin, A.S. et al.: Synthesis and structural characterization of a series of novel polyaromatic ligands containing pyrene and related biscyclometalated iridium complexes. Organometallics, vol. 25, pp. 1461-1471, 2006.
Xin Li et al., "Density functional theory study of photophysical properties of iridium (III) complexes with phenylisoquinoline and phenylpyridine ligands", The Journal of Physical Chemistry C, 2011, vol. 115, No. 42, pp. 20722-20731.
Sylvia Bettington et al. "Tris-Cyclometalated Iridium(lll) Complexes of Carbazole(fluorenyl)pyridine Ligands: Synthesis, Redox and Photophysical Properties, and Electrophosphorescent Light-Emitting Diodes" Chemistry: A European Journal, 2007, vol. 13, pp. 1423-1431.
Christoph Ulbricht et al., "Synthesis and Characterization of Oxetane-Functionalized Phosphorescent Ir(lll)-Complexes", Macromol. Chem. Phys. 2009, 2010, pp. 531-541.
Dan Wang et al., "Carbazole and arylamine functionalized iridium complexes for efficient electro-phosphorescent light-emitting diodes", Inorganica Chimica Acta 370 (2011) pp. 340-345.
Huaijun Tang et al., "Novel yellow phosphorescent iridium complexes containing a carbazoleeoxadioazole unit used in polymeric light-emitting diodes", Dyes and Pigments 91 (2011) pp. 413-421.
Hoe-Joo Seo et al., "Blue phosphorescent iridium(lll) complexes containing carbazole-functionalized phenyl pyridine for organic light-emitting diodes: energy transfer from carbazolyl moieties to iridium(lll) cores", RSC Advances, 2011, vol. 1, pp. 755-757.
Jack W. Levell et al., "Carbazole/iridium dendrimer side-chain phosphorescent copolymers for efficient light emitting devices", New J. Chem., 2012, vol. 36, pp. 407-413.
Z Liu et al., "Green and blue-green phosphorescent heteroleptic iridium complexes containing carbazole-functionalized beta-diketonate for non-doped organic light-emitting diodes", Organic Electronics 9 (2008) pp. 171-182.
Zhaowu Xu et al., "Synthesis and properties of iridium complexes based on 1,3,4-oxadiazoles derivatives", Tetrahedron 64 (2008) pp. 1860-1867.
Kwon-Hyeon Kim et al., "Controlling Emitting Dipole Orientation with Methyl Substituents on Main Ligand of Iridium Complexes for Highly Efficient Phosphorescent Organic Light-Emitting Diodes", Adv. Optical Mater. 2015, 3, pp. 1191-1196.
Matthew J. Jurow et al., "Understanding and predicting the orientation of heteroleptic phosphors in organic light-emitting materials", Nature Materials, vol. 15, Jan. 2016, pp. 85-93.

\* cited by examiner

CHIRAL METAL COMPLEXES AS EMITTERS FOR ORGANIC POLARIZED ELECTROLUMINESCENT DEVICES

CROSS-REFERENCE TO RELATED APPLICATIONS

This application is a U.S. National Phase Application of International Patent Application No. PCT/US2015/018195 filed Feb. 27, 2015, which claims the benefit of U.S. Provisional Application Ser. No. 61/945,940 entitled "CHIRAL METAL COMPLEXES AS EMITTERS FOR ORGANIC POLARIZED ELECTROLUMINESCENT DEVICES" and filed on Feb. 28, 2014, the contents of both of which are incorporated herein by reference in their entirety.

TECHNICAL FIELD

This description relates to chiral metal complexes as emitters for organic polarized electroluminescent devices.

BACKGROUND

Organic light emitting devices (OLEDs) are a new generation of display technology. As depicted in FIG. 1, a typical OLED 100 includes a layer of indium tin oxide (ITO) as an anode 102, a single layer of hole-transporting materials (HTL) 104, a single layer of emissive materials (EML) 106 including emitter and host, a single layer of electron-transporting materials (ETL) 108 and a layer of metal cathode 110. The emission color of OLED is determined by the emission energy (optical energy gap) of emitters. Emitters include phosphorescent emitters, thermal activated delayed fluorescent emitters, and metal-assisted delayed fluorescent emitters.

OLEDs with polarized electroluminescent spectra are desirable for mobile displays or other full color display applications. To enable a high quality of full color displays, a polarizer may be coupled to a transparent electrode of an OLED to filter unwanted reflected light from the background, thereby yielding linearly or circularly polarized light. FIG. 2A depicts a linearly polarized light wave 200. FIG. 2B depicts a circularly polarized light wave 202. This polarizer/OLED arrangement, however, decreases the device efficiency of the OLED by filtering some of the emitted photons.

SUMMARY

Chiral metal complex emitters provide various advantages over non-polarized emitters with respect to organic polarized electroluminescent devices. For example, chiral metal complex emitters generate polarized electroluminescent spectra without the use of polarizers, thereby eliminating photon loss due to the polarizers. Specific alignment of chiral metal complex emitters may also reduce the plasmon quenching from the metal electrode and enhance the outcoupling efficiency of the device, thereby allowing more photons to exit the device and resulting in a higher illumination intensity.

Disclosed herein is an organometallic complex of general formula (1),

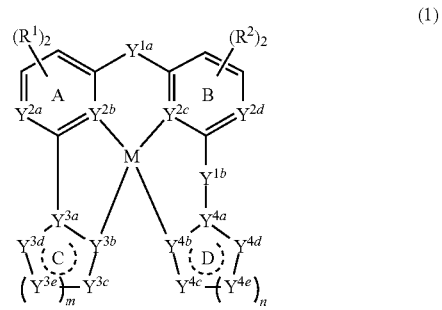

wherein:

M is a metal ion;

each $R^1$ and $R^2$ is independently selected from hydrogen, halogen, hydroxyl, amino, nitro, thiol, and substituted or unsubstituted $C_1$-$C_4$ alkyl;

$Y^{1a}$, when present, is selected from the group consisting of a direct bond, O, S, $NR^{3a}$, $BR^{3a}$, $Si(R^{3b})_2$, or $C(R^{3c})_2$;

each $R^{3a}$ is independently selected from substituted or unsubstituted $C_1$-$C_4$ alkyl;

each $R^{3b}$ is independently selected from substituted or unsubstituted $C_1$-$C_4$ alkyl;

each $R^{3c}$ is independently selected from hydrogen and substituted or unsubstituted $C_1$-$C_4$ alkyl;

$Y^{1b}$ when present, is selected from the group consisting of a direct bond, O, S, $NR^{4a}$, $BR^{4a}$, $Si(R^{4b})_2$, and $C(R^{4c})_2$;

each $R^{4a}$ is independently selected from substituted or unsubstituted $C_1$-$C_4$ alkyl;

each $R^{4b}$ is independently selected from substituted or unsubstituted $C_1$-$C_4$ alkyl;

each $R^{4c}$ is independently selected from hydrogen and substituted or unsubstituted $C_1$-$C_4$ alkyl;

each $Y^{2a}$, $Y^{2b}$, $Y^{2c}$, and $Y^{2b}$ is independently selected from the group consisting of O, S, N, $NR^{5a}$, $BR^{5a}$, C, and $CR^{5b}$;

each $R^{5a}$ and $R^{5b}$ is independently selected from the group consisting of hydrogen, halogen, hydroxyl, amino, nitro, thiol, and substituted or unsubstituted $C_1$-$C_4$ alkyl;

each $Y^{3a}$, $Y^{3b}$, $Y^{3c}$, $Y^{3d}$, $Y^{3e}$, $Y^{4a}$, $Y^{4b}$, $Y^{4c}$, $Y^{4d}$, and $Y^{4e}$ is independently selected from the group consisting of N, O, S, $NR^{6a}$, $BR^{6a}$ $CR^{6b}$, and $Z(R^{6c})_2$;

Z is C or Si;

each $R^{6a}$ and $R^{6b}$ is independently selected from hydrogen and substituted or unsubstituted $C_1$-$C_4$ alkyl;

each $R^{6c}$ is independently selected from hydrogen and substituted or unsubstituted $C_1$-$C_4$ alkyl;

m is 1 or 2;

n is 1 or 2;

represents partial or full unsaturation of the ring with which it is associated;

each ring A, B, C, and D is independently optionally fused to one or two independently selected $C_{3-6}$ cycloalkyl, $C_{6-10}$ aryl, or 4-10 membered heterocycloalkyl groups; and at least one of M, $R^1$, $R^2$, $R^3$, $Y^{1a}$, $Y^{1b}$, $Y^{2a}$, $Y^{2b}$, $Y^{2c}$, $Y^{2d}$, $Y^{3a}$, $Y^{3b}$, $Y^{3c}$, $Y^{3d}$, $Y^{3e}$, $Y^{4a}$, $Y^{4b}$, $Y^{4c}$, $Y^{4d}$ and $Y^{4e}$ is a chiral center or comprises one or more chiral centers.

The present disclosure also provides an organometallic complex of general formula (2), (2)

[Chemical structure diagram of formula (2) showing metal complex with rings A, B, C, D, substituents $(R^1)_2$, $(R^2)_2$, and various Y positions around central metal M]

wherein:

M is a metal ion;

each $R^1$ and $R^2$ is independently selected from the group consisting of hydrogen, halogen, hydroxyl, amino, nitro, thiol, and substituted or unsubstituted $C_1$-$C_4$ alkyl;

$Y^{1a}$, when present, is selected from the group consisting of a direct bond, O, S, $NR^{3a}$, $BR^{3a}$, $Si(R^{3b})_2$, and $C(R^{3c})_2$;

each $R^{3a}$ is independently selected from substituted or unsubstituted $C_1$-$C_4$ alkyl;

each $R^{3b}$ is independently selected from substituted or unsubstituted $C_1$-$C_4$ alkyl;

each $R^{3c}$ is independently selected from hydrogen and substituted or unsubstituted $C_1$-$C_4$ alkyl;

$Y^{1b}$, when present, is selected from the group consisting of a direct bond, O, S, $NR^{4a}$, $BR^{4a}$, $Si(R^{4b})_2$, and $C(R^{4c})_2$;

each $R^{4a}$ is independently selected from substituted or unsubstituted $C_1$-$C_4$ alkyl;

each $R^{4b}$ is independently selected from substituted or unsubstituted $C_1$-$C_4$ alkyl;

each $R^{4c}$ is independently selected from hydrogen and substituted or unsubstituted $C_1$-$C_4$ alkyl;

$Y^{1c}$, when present, is selected from the group consisting of a direct bond, O, S, $NR^{5a}$, $BR^{5a}$, $Si(R^{5b})_2$, and $C(R^{5c})_2$;

each $R^{5a}$ is independently selected from substituted or unsubstituted $C_1$-$C_4$ alkyl;

each $R^{5b}$ is independently selected from substituted or unsubstituted $C_1$-$C_4$ alkyl;

each $R^{5c}$ is independently selected from hydrogen and substituted or unsubstituted $C_1$-$C_4$ alkyl;

each $Y^{2a}$, $Y^{2b}$, $Y^{2c}$, and $Y^{2d}$ is independently selected from the group consisting of O, S, N, $NR^{6a}$, $BR^{6a}$, and $CR^{6b}$;

each $R^{6a}$ and $R^{6b}$ is independently selected from the group consisting of hydrogen, halogen, hydroxyl, amino, nitro, thiol, substituted or unsubstituted $C_1$-$C_4$ alkyl;

each $Y^{3a}$, $Y^{3b}$, $Y^{3c}$, $Y^{3d}$, $Y^{3e}$, $Y^{4a}$, $Y^{4b}$, $Y^{4c}$, $Y^{4d}$, and $Y^{4e}$ is independently selected from the group consisting of N, O, S, $NR^{7a}$, $BR^{7a}$, $CR^{7b}$, and $Z(R^{7c})_2$;

Z is C or Si;

each $R^{7a}$ and $R^{7b}$ is independently selected from hydrogen and substituted or unsubstituted $C_1$-$C_4$ alkyl;

each $R^{7c}$ is independently selected from hydrogen and substituted or unsubstituted $C_1$-$C_4$ alkyl;

m is 1 or 2;

n is 1 or 2;

$\begin{pmatrix} \vdots \\ \end{pmatrix}$ represents partial or full unsaturation of the ring with which it is associated;

each ring A, B, C, and D is independently optionally fused to one or two independently selected $C_{3-6}$ cycloalkyl, $C_{6-10}$ aryl, or 4-10 membered heterocycloalkyl groups; and at least one of M, $R^1$, $R^2$, $Y^{1a}$, $Y^{1b}$, $Y^{1c}$, $Y^{2a}$, $Y^{2b}$, $Y^{2c}$, $Y^{2d}$, $Y^{3a}$, $Y^{3b}$, $Y^{3c}$, $Y^{3d}$, $Y^{3e}$, $Y^{4a}$, $Y^{4b}$, $Y^{4c}$, $Y^{4d}$, and $Y^{4e}$ is a chiral center or comprises one or more chiral centers.

The present disclosure also provides an organometallic complex of general formula (3), (3)

[Chemical structure diagram of formula (3) showing metal complex with rings A, B, C, D, E, F, substituents $(R^1)_2$, $(R^2)_2$, and various Y positions around central metal M]

wherein:

M is a metal ion;

each $R^1$ and $R^2$ is independently selected from the group consisting of hydrogen, halogen, hydroxyl, amino, nitro, thiol, and substituted or unsubstituted $C_1$-$C_4$ alkyl;

each $Y^{2a}$, $Y^{2b}$, $Y^{2c}$, and $Y^{2d}$ is independently selected from the group consisting of O, S, N, $NR^{3a}$, $BR^{3a}$, and $CR^{3b}$;

each $R^{3a}$ and $R^{3b}$ is independently selected from the group consisting of hydrogen, halogen, hydroxyl, amino, nitro, thiol, and substituted or unsubstituted $C_1$-$C_4$ alkyl;

each $Y^{3a}$, $Y^{3b}$, $Y^{3c}$, $Y^{3d}$, $Y^{3e}$, $Y^{4a}$, $Y^{4b}$, and $Z(R^{4c})_2$; the group consisting of N, O, S, $NR^{4a}$, $BR^{4a}$, $CR^{4b}$, and $Z(R^{4c})_2$;

Z is C or Si;

each $R^{4a}$ and $R^{4b}$ is independently selected from hydrogen and substituted or unsubstituted $C_1$-$C_4$ alkyl;

each $R^{4c}$ is independently selected from hydrogen and substituted or unsubstituted $C_1$-$C_4$ alkyl;

m is 1 or 2;

n is 1 or 2;

l is 1 or 2;

o is 1 or 2;

$\begin{pmatrix} \vdots \\ \end{pmatrix}$ represents partial or full unsaturation of the ring with which it is associated;

$Y^{5a}$, $Y^{5b}$, $Y^{5c}$, $Y^{5d}$, $Y^{5e}$, $Y^{6a}$, $Y^{6b}$, $Y^{6c}$, $Y^{6d}$, and $Y^{6e}$ is independently selected from the group consisting of N, O, S, $NR^{6a}$, and $CR^{6b}$;

each ring A, B, C, D, E, and F is independently optionally fused to one or two independently selected $C_{3-6}$ cycloalkyl, $C_{6-10}$ aryl, or 4-10 membered heterocycloalkyl groups; and at least one of M, $R^1$, $R^2$, $Y^{2a}$, $Y^{2b}$, $Y^{2c}$, $Y^{2d}$, $Y^{3a}$, $Y^{3b}$, $Y^{3c}$, $Y^{3d}$, $Y^{3e}$, $Y^{4a}$, $Y^{4b}$, $Y^{4c}$, $Y^{4d}$, $Y^{4e}$, $Y^{5a}$, $Y^{5b}$, $Y^{5c}$, $Y^{5d}$, $Y^{5e}$, $Y^{6a}$, $Y^{6b}$, $Y^{6c}$, $Y^{6d}$, and $Y^{6e}$ is a chiral center or comprises one or more chiral centers.

The present disclosure further provides an organometallic complex of general formula (4),

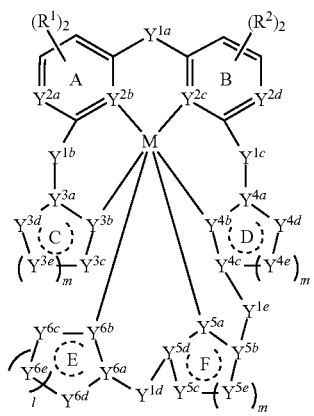

(4)

wherein:

M is a metal ion;

each $R^1$ and $R^2$ is independently selected from the group consisting of hydrogen, halogen, hydroxyl, amino, nitro, thiol, and substituted or unsubstituted $C_1$-$C_4$ alkyl;

$Y^{1a}$ is selected from the group consisting of O, S, $NR^{4a}$, $BR^{4a}$, $Si(R^{4b})_2$, and $C(R^{4c})_2$, $R^{4a}$ is substituted or unsubstituted $C_1$-$C_4$ alkyl;

each $R^{4b}$ is independently selected from substituted or unsubstituted $C_1$-$C_4$ alkyl;

each $R^{4c}$ is independently selected from hydrogen and substituted or unsubstituted $C_1$-$C_4$ alkyl;

$Y^{1b}$ is selected from the group consisting of O, S, $NR^{5a}$, $BR^{5a}$, $Si(R^{5b})_2$, and $C(R^{5e})_2$, $R^{5a}$ is substituted or unsubstituted $C_1$-$C_4$ alkyl;

each $R^{5b}$ is independently selected from substituted and unsubstituted $C_1$-$C_4$ alkyl;

each $R^{5c}$ is independently selected from hydrogen and substituted or unsubstituted $C_1$-$C_4$ alkyl;

$Y^{1c}$ is selected from the group consisting of O, S, $NR^{4a}$, $BR^{4a}$, $Si(R^{4b})_2$, and $C(R^{4c})_2$;

$R^{4a}$ is substituted or unsubstituted $C_1$-$C_4$ alkyl;

each $R^{4b}$ is independently selected from substituted and unsubstituted $C_1$-$C_4$ alkyl;

each $R^{4c}$ is independently selected from hydrogen and substituted or unsubstituted $C_1$-$C_4$ alkyl;

$Y^{1d}$ is selected from the group consisting of O, S, $NR^{4a}$, $BR^{4b}$, $Si(R^{4b})_2$, and $C(R^{4c})_2$;

$R^{4a}$ is substituted or unsubstituted $C_1$-$C_4$ alkyl;

each $R^{4b}$ is independently selected from substituted and unsubstituted $C_1$-$C_4$ alkyl;

each $R^{4c}$ is independently selected from hydrogen and substituted or unsubstituted $C_1$-$C_4$ alkyl;

$Y^{1e}$, when present, is selected from the group consisting of a direct bond, O, S, $NR^{4a}$, $BR^{4a}$, $Si(R^{4b})_2$, and $C(R^{3c})_2$;

$R^{4a}$ is substituted or unsubstituted $C_1$-$C_4$ alkyl;

each $R^{4b}$ is independently selected from substituted and unsubstituted $C_1$-$C_4$ alkyl;

each $R^{4c}$ is independently selected from hydrogen and substituted or unsubstituted $C_1$-$C_4$ alkyl;

each $Y^{2a}$, $Y^{2b}$, $Y^{2c}$, and $Y^{2d}$ is independently selected from the group consisting of O, S, N, $NR^{6a}$, $BR^{6a}$, and $CR^{6b}$;

each $R^{6a}$ and $R^{6b}$ is independently selected from the group consisting of hydrogen, halogen, hydroxyl, amino, nitro, thiol, and substituted or unsubstituted $C_1$-$C_4$ alkyl;

each $Y^{3a}$, $Y^{3b}$, $Y^{3c}$, $Y^{3d}$, $Y^{3e}$, $Y^{4a}$, $Y^{4b}$, $Y^{4c}$, $Y^{4d}$, and $Y^{4e}$ is independently selected from the group consisting of N, O, S, $NR^{6a}$, $BR^{6a}$, $CR^{6b}$, and $Z(R^{6c})_2$;

Z is C or Si;

each $R^{6a}$ and $R^{6b}$ is independently selected from hydrogen and substituted or unsubstituted $C_1$-$C_4$ alkyl;

each $R^{6c}$ is independently selected from hydrogen and substituted or unsubstituted $C_1$-$C_4$ alkyl;

each m is independently 1 or 2;

represents partial or full unsaturation of the ring with which it is associated;

each $Y^{5a}$, $Y^{5b}$, $Y^{5c}$, $Y^{5d}$, $Y^{5e}$, $Y^{6a}$, $Y^{6b}$, $Y^{6c}$, $Y^{6d}$, and $Y^{6e}$ is independently selected from the group consisting of N, O, S, $NR^{6a}$, and $CR^{6b}$;

each ring A, B, C, D, E, and F is independently optionally fused to one or two independently selected $C_{3-6}$ cycloalkyl, $C_{6-10}$ aryl, or 4-10 membered heterocycloalkyl groups; and at least one of M, $R^1$, $R^2$, $Y^{1a}$, $Y^{1b}$, $Y^{1c}$, $Y^{1d}$, $Y^{1e}$, $Y^{2a}$, $Y^{2b}$, $Y^{2c}$, $Y^{2d}$, $Y^{3a}$, $Y^{3b}$, $Y^{3c}$, $Y^{3d}$, $Y^{3e}$, $Y^{4a}$, $Y^{4b}$, $Y^{4c}$, $Y^{4d}$, $Y^{4e}$, $Y^{5a}$, $Y^{5b}$, $Y^{5c}$, $Y^{5d}$, $Y^{5e}$, $Y^{6a}$, $Y^{6b}$, $Y^{6c}$, $Y^{6d}$, and $Y^{6e}$ is a chiral center or comprises one or more chiral centers.

Also disclosed herein are compositions including one or more chiral metal complexes disclosed herein.

Also disclosed herein are devices, such as OLEDs, including one or more chiral metal complexes disclosed herein.

Thus, particular embodiments have been described. Variations, modifications, and enhancements of the described embodiments and other embodiments can be made based on what is described and illustrated. In addition, one or more features of one or more embodiments may be combined. The details of one or more implementations and various features and aspects are set forth in the accompanying drawings, the description, and the claims below.

BRIEF DESCRIPTION OF THE DRAWINGS

FIGS. 14A and 4B depict chiral isomers of an octahedral metal complex.

DETAILED DESCRIPTION

Figure 1:
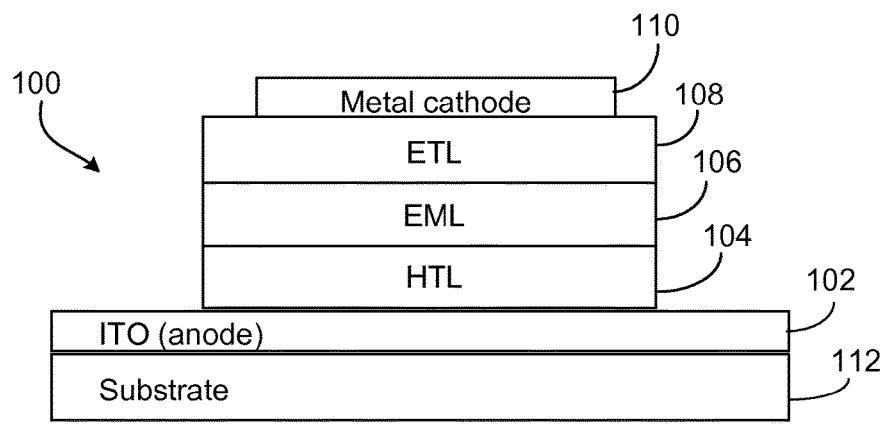
FIG. 1 depicts an organic light emitting device (OLED).
Figure 2A:
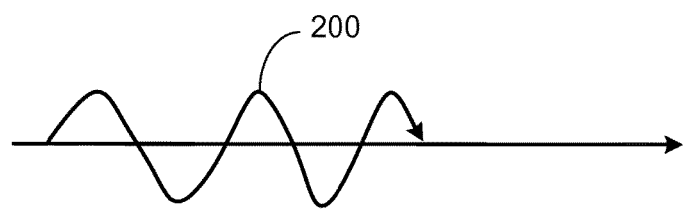
FIGS. 2A and 2B depict linearly polarized and circularly polarized light waves, respectively.
Figure 2B:
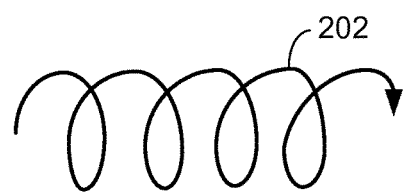

The present disclosure can be understood more readily by reference to the following detailed description and Examples.

Before the present compounds, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing, example methods and materials are now described.

As used in the specification and the appended claims, the singular forms "a", "an", and "the" include plural referents unless the context clearly dictates otherwise. Thus, for example, reference to "a component" includes mixtures of two or more components.

As used herein, the terms "optional" and "optionally" mean that the subsequently described event or circumstance can or cannot occur, and that the description includes instances where said event or circumstance occurs and instances where it does not.

Disclosed are the components to be used to prepare the compositions described herein as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions. Thus, if there are a variety of additional steps that can be performed it is understood that each of these additional steps can be performed with any specific embodiment or combination of embodiments of the methods.

As referred to herein, a linking atom or group connects two atoms such as, for example, a N atom and a C atom. The linking atom or group can optionally, if valency permits, have other chemical moieties attached. For example, in one aspect, an oxygen would not have any other chemical groups attached as the valency is satisfied once it is bonded to two groups (e.g., N and/or C groups). In another aspect, when carbon is the linking atom, two additional chemical moieties can be attached to the carbon. Suitable chemical moieties include, for example, amine, amide, thiol, aryl, heteroaryl, cycloalkyl, and heterocyclyl.

The term "cyclic structure" or the like terms used herein refer to any cyclic chemical structure which includes, but is not limited to, aryl, heteroaryl, cycloalkyl, cycloalkenyl, heterocyclyl, carbene, and N-heterocyclic carbene.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$-OA$^2$ or —OA$^1$-(OA$^2$)$_a$-OA$^3$, where "a" is an integer of from 1 to 200 and A$^1$, A$^2$, and A$^3$ are alkyl and/or cycloalkyl groups.

The term "aldehyde" as used herein is represented by the formula —C(O)H. Throughout this specification "C(O)" is a short hand notation for a carbonyl group, i.e., C=O.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The terms "amine" or "amino" as used herein are represented by the formula —NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl. In some aspects, an aryl group has from 6 to 20 carbons. In some aspects, an aryl group has from 6 to 10 carbons.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. In some aspects, a cycloalkyl group comprises 3 to 20 carbons. In some aspects, a cycloalkyl group comprises 3 to 10 atoms carbons. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein. In some aspects, a heterocycloalkyl group comprises from 4 to 10 atoms (e.g., C, N, S, and O). In some aspects, a heterocycloalkyl group comprises 4 to 10 atoms (e.g., C, N, S, and O).

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "halogen" as used herein refers to the halogens fluorine, chlorine, bromine, and iodine.

The term "heterocyclyl," as used herein refers to single and multi-cyclic non-aromatic ring systems and "heteroaryl as used herein refers to single and multi-cyclic aromatic ring systems: in which at least one of the ring members is other than carbon. The terms includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5- tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "nitro" as used herein is represented by the formula —$NO_2$.

The term "thiol" as used herein is represented by the formula —SH.

The term "nitrile" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulae —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

"R," "$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Compounds described herein may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

In some aspects, a structure of a compound can be represented by a formula:

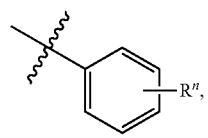

which is understood to be equivalent to a formula:

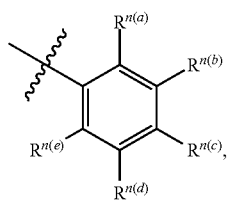

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Several references to variables (e.g., $R^1$, M, $Y^{1a}$, $Y^{1b}$, etc.) are made in chemical structures and moieties disclosed and described herein. Any description of variables in the specification is applicable to any structure or moiety reciting said variables, respectively.

The following abbreviations may be used herein: aq. (aqueous); calc. (calculated); d (doublet); dd (doublet of doublets); DCM (dichloromethane); DMF (N ,N-dimethylformamide); DMSO (dimethyl sulfoxide) eq. (equivalents); Et (ethyl); EtOAc (ethyl acetate); g (gram(s)); h (hour(s)); Hz (hertz); HCl (hydrochloric acid/hydrogen choride); HPLC (high performance liquid chromatography); J (coupling constant); $K_2PtCl_4$ (potassium tetrachloroplatinate); m (multiplet); MHz (megahertz); MS (Mass spectrometry); Me (methyl); mg (milligram(s)); min (minutes(s)); mL (milliliter(s)); mmol (millimole(s)); mol % (mole percent); $^nBu$ (n-butyl); $^nBu_4NBr$ (tetra-n-butylammonium bromide); NMR (nuclear magnetic resonance spectroscopy); Pd (palladium); pM (picomolar); s (singlet); t (triplet or tertiary); μg (microgram(s)); μL (microliter(s)); μM (micromolar); wt % (weight percent).

Compounds

Figure 3A:
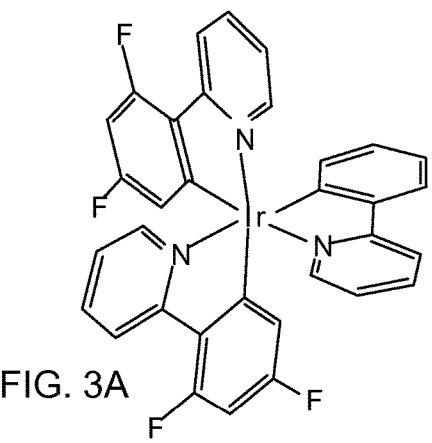
FIGS. 3A and 3B depict chiral isomers of an octahedral metal complex.
Figure 3B:
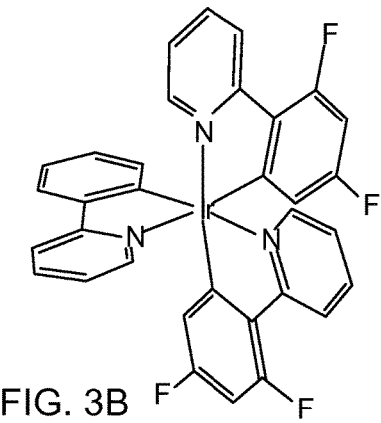

A chiral structure, such as a molecule or organometallic complex, is not superimposable on its mirror image. FIGS. 3A and 3B depict chiral isomers of an octahedral metal complex. A chiral center is an atom in a structure, such as an organic molecule, that has four or more unique atoms or groups attached to it.

Figure 4A:
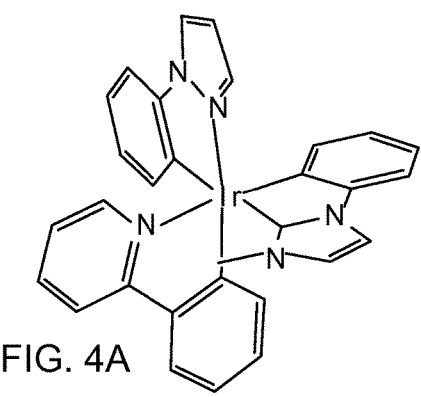
FIGS. 4A-4D depict structures with chiral centers.
Figure 4B:
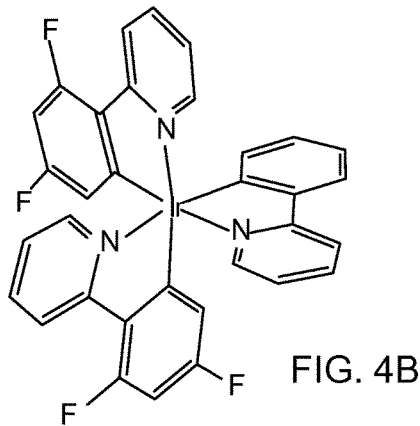
Figure 4C:
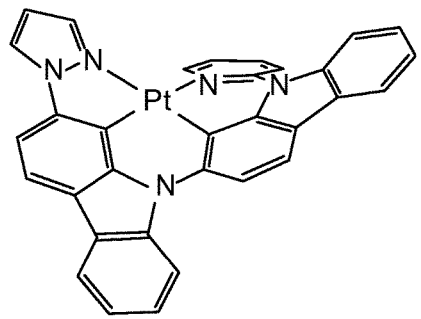
Figure 4D:
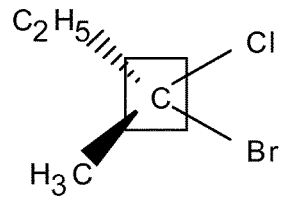
Figure 5A:
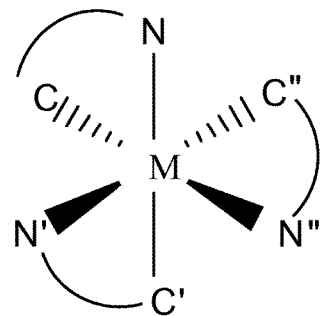
FIGS. 5A-5D depict general schemes for chiral metal complex based emitters.
Figure 5B:
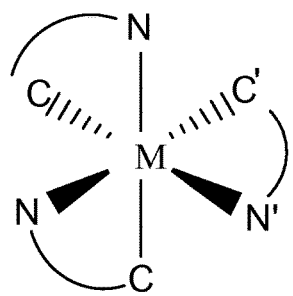
Figure 5C:
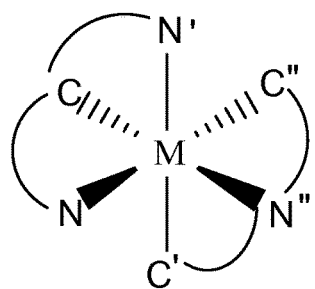
Figure 5D:
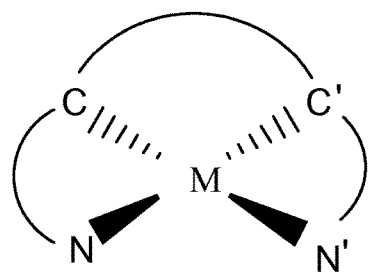

Examples of chiral centers are shown in FIGS. 4A-4D, 9A, 9B, 14A, and 14B. In FIGS. 4A, 4B, 9A, 9B, 14A, and 14B, the iridium is a chiral center. In FIG. 4C, the platinum is a chiral center. In FIG. 4D, the carbon is a chiral center.

FIGS. 4A-4C depict three classes of chiral metal complexes. FIG. 4A depicts an octahedral metal complex with three different cyclometalating ligands (e.g., Ir(CN)(C'N') (C"N")). FIG. 4B depicts an octahedral metal complex with two different cyclometalating ligands, i.e. Ir(CN)$_2$(C'N'). FIG. 4C depicts a non-planar asymmetric tetrahedral metal complex.

FIGS. 5A-5D depict general schemes for chiral metal complex based emitters, where at least one of M or other functional group such as C, C', C", N, N', and N" includes one or more chiral centers.

The present disclosure provides an organometallic complex of general formula (1),

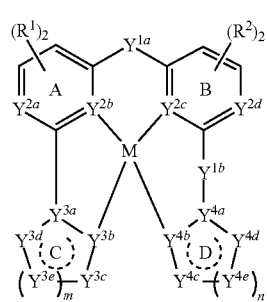

(1)

wherein:

M is a metal ion;

each $R^1$ and $R^2$ is independently selected from hydrogen, halogen, hydroxyl, amino, nitro, thiol, and substituted or unsubstituted $C_1$-$C_4$ alkyl;

$Y^{1a}$, when present, is selected from the group consisting of a direct bond, O, S, $NR^{3a}$, $BR^{3a}$, $Si(R^{3b})_2$, or $C(R^{3c})_2$;

each $R^{3a}$ is independently selected from substituted or unsubstituted $C_1$-$C_4$ alkyl;

each $R^{3b}$ is independently selected from substituted or unsubstituted $C_1$-$C_4$ alkyl;

each $R^{3c}$ is independently selected from hydrogen and substituted or unsubstituted $C_1$-$C_4$ alkyl;

$Y^{1b}$, when present, is selected from the group consisting of a direct bond, O, S, $NR^{4a}$, $BR^{4a}$, $Si(R^{4b})_2$, and $C(R^{4c})_2$;

each $R^{4a}$ is independently selected from substituted or unsubstituted $C_1$-$C_4$ alkyl;

each $R^{4b}$ is independently selected from substituted or unsubstituted $C_1$-$C_4$ alkyl;

each $R^{4c}$ is independently selected from hydrogen and substituted or unsubstituted $C_1$-$C_4$ alkyl;

$Y^{2a}$, $Y^{2b}$, $Y^{2c}$, and $Y^{2d}$ is independently selected from the group consisting of O, S, N, $NR^{5a}$, $BR^{5a}$, C, and $CR^{5b}$;

each $R^{5a}$ and $R^{5b}$ is independently selected from the group consisting of hydrogen, halogen, hydroxyl, amino, nitro, thiol, and substituted or unsubstituted $C_1$-$C_4$ alkyl;

each $Y^{3a}$, $Y^{3b}$, $Y^{3c}$, $Y^{3d}$, $Y^{3e}$, $Y^{4a}$, $Y^{4b}$, $Y^{4c}$, $Y^{4d}$, and $Y^{4e}$ is independently selected from the group consisting of N, O, S, $NR^{6a}$, $BR^{6a}$ $CR^{6b}$, and $Z(R^{6c})_2$;

Z is C or Si;

each $R^{6a}$ and $R^{6b}$ is independently selected from hydrogen and substituted or unsubstituted $C_1$-$C_4$ alkyl;

each $R^{6c}$ is independently selected from hydrogen and substituted or unsubstituted $C_1$-$C_4$ alkyl;

m is 1 or 2;

n is 1 or 2;

'- -' represents partial or full unsaturation of the ring with which it is associated;

each ring A, B, C, and D is independently optionally fused to one or two independently selected $C_{3-6}$ cycloalkyl, $C_{6-10}$ aryl, or 4-10 membered heterocycloalkyl groups; and at least one of M, $R^1$, $R^2$, $Y^{1a}$, $Y^{1b}$, $Y^{2a}$, $Y^{2b}$, $Y^{2c}$, $Y^{2d}$, $Y^{3a}$, $Y^{3b}$, $Y^{3c}$, $Y^{3d}$, $Y^{3e}$, $Y^{4a}$, $Y^{4b}$, $Y^{4c}$, $Y^{4d}$ and $Y^{4e}$ includes one or more chiral centers.

The present disclosure also provides an organometallic complex of general formula (2),

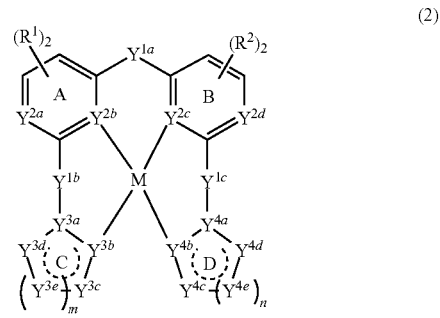

(2)

wherein:

M is a metal ion;

each $R^1$ and $R^2$ is independently selected from the group consisting of hydrogen, halogen, hydroxyl, amino, nitro, thiol, and substituted or unsubstituted $C_1$-$C_4$ alkyl;

$Y^{1a}$, when present, is selected from the group consisting of a direct bond, O, S, $NR^{3a}$, $BR^{3a}$, $Si(R^{3b})_2$, and $C(R^{3c})_2$, each $R^{3a}$ is independently selected from substituted or unsubstituted $C_1$-$C_4$ alkyl;

each $R^{3b}$ is independently selected from substituted or unsubstituted $C_1$-$C_4$ alkyl;

each $R^{3c}$ is independently selected from hydrogen and substituted or unsubstituted $C_1$-$C_4$ alkyl;

$Y^{1b}$, when present, is selected from the group consisting of a direct bond, O, S, $NR^{4a}$, $BR^{4a}$, $Si(R^{4b})_2$, and $C(R^{4c})_2$;

each $R^{4a}$ is independently selected from substituted or unsubstituted $C_1$-$C_4$ alkyl;

each $R^{4b}$ is independently selected from substituted or unsubstituted $C_1$-$C_4$ alkyl;

each $R^{4c}$ is independently selected from hydrogen and substituted or unsubstituted $C_1$-$C_4$ alkyl;

$Y^{1c}$, when present, is selected from the group consisting of a direct bond, O, S, $NR^{5a}$, $BR^{5a}$, $Si(R^{5b})_2$, and $C(R^{5c})_2$;

each $R^{5a}$ is independently selected from substituted or unsubstituted $C_1$-$C_4$ alkyl;

each $R^{5b}$ is independently selected from substituted or unsubstituted $C_1$-$C_4$ alkyl;

each $R^{5c}$ is independently selected from hydrogen and substituted or unsubstituted $C_1$-$C_4$ alkyl;

each $Y^{2a}$, $Y^{2b}$, $Y^{2c}$, and $Y^{2d}$ is independently selected from the group consisting of O, S, N, $NR^{6a}$, $BR^{6a}$, and $CR^{6b}$;

each $R^{6a}$ and $R^{6b}$ is independently selected from the group consisting of hydrogen, halogen, hydroxyl, amino, nitro, thiol, and substituted or unsubstituted $C_1$-$C_4$ alkyl;

each $Y^{3a}$, $Y^{3b}$, $Y^{3c}$, $Y^{3e}$, $Y^{4a}$, $Y^{4b}$, $Y^{4c}$, $Y^{4d}$, and $Y^{4e}$ is independently selected from the group consisting of N, O, S, $NR^{7a}$, $BR^{7a}$, $CR^{7b}$, and $Z(R^{7c})_2$;

Z is C or Si;

each $R^{7a}$ and $R^{7b}$ is independently selected from hydrogen and substituted or unsubstituted $C_1$-$C_4$ alkyl;

each $R^{7c}$ is independently selected from hydrogen and substituted or unsubstituted $C_1$-$C_4$ alkyl;

m is 1 or 2;

n is 1 or 2;

$\binom{\cdot}{\cdot\_\cdot}$ represents partial or full unsaturation of the ring with which it is associated;

each ring A, B, C, and D is independently optionally fused to one or two independently selected $C_{3-6}$ cycloalkyl, $C_{6-10}$ aryl, or 4-10 membered heterocycloalkyl groups; and at least one of M, $R^1$, $R^2$, $Y^{1a}$, $Y^{1b}$, $Y^{1c}$, $Y^{2a}$, $Y^{2b}$, $Y^{2c}$, $Y^{2d}$, $Y^{3a}$, $Y^{3b}$, $Y^{3c}$, $Y^{3d}$, $Y^{3e}$, $Y^{4a}$, $Y^{4b}$, $Y^{4c}$, $Y^{4d}$, and $Y^{4e}$ is a chiral center or comprises one or more chiral centers.

The present disclosure also provides an organometallic complex of general formula (3),

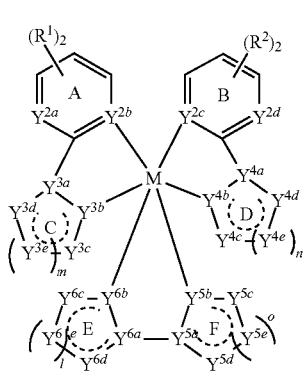

(3)

wherein:
M is a metal ion;
each $R^1$ and $R^2$ is independently selected from the group consisting of hydrogen, halogen, hydroxyl, amino, nitro, thiol, and substituted or unsubstituted $C_1$-$C_4$ alkyl;

each $Y^{2a}$, $Y^{2b}$, $Y^{2c}$, and $Y^{2d}$ is independently selected from the group consisting of O, S, N, $NR^{3a}$, $BR^{3a}$, and $CR^{3b}$;

each $R^{3a}$ and $R^{3b}$ is independently selected from the group consisting of hydrogen, halogen, hydroxyl, amino, nitro, thiol, and substituted or unsubstituted $C_1$-$C_4$ alkyl;

each $Y^{3a}$, $Y^{3b}$, $Y^{3c}$, $Y^{3d}$, $Y^{3e}$, $Y^{4a}$, $Y^{4b}$, $Y^{4c}$, $Y^{4d}$, and $Y^{4e}$ is independently selected from the group consisting of N, O, S, $NR^{4a}$, $BR^{4a}$, $CR^{4b}$, and $Z(R^{4c})_2$;

Z is C or Si;

each $R^{4a}$ and $R^{4b}$ is independently selected from hydrogen and substituted or unsubstituted $C_1$-$C_4$ alkyl;

each $R^{4c}$ is independently selected from hydrogen and substituted or unsubstituted $C_1$-$C_4$ alkyl;

m is 1 or 2;
n is 1 or 2;
l is 1 or 2;
o is 1 or 2;

$\binom{\cdot}{\cdot\_\cdot}$ represents partial or full unsaturation of the ring with which it is associated;

each $Y^{5a}$, $Y^{5b}$, $Y^{5c}$, $Y^{5d}$, $Y^{5e}$, $Y^{6a}$, $Y^{6b}$, $Y^{6c}$, $Y^{6d}$, and $Y^{6e}$ is independently selected from the group consisting of N, O, S, $NR^{6a}$, and $CR^{6b}$;

each ring A, B, C, D, E, and F is independently optionally fused to one or two independently selected $C_{3-6}$ cycloalkyl, $C_{6-10}$ aryl, or 4-10 membered heterocycloalkyl groups; and at least one of M, $R^1$, $R^2$, $Y^{2a}$, $Y^{2b}$, $Y^{2c}$, $Y^{2d}$, $Y^{3a}$, $Y^{3b}$, $Y^{3c}$, $Y^{3d}$, $Y^{3e}$, $Y^{4a}$, $Y^{4b}$, $Y^{4c}$, $Y^{4d}$, $Y^{4e}$, $Y^{5a}$, $Y^{5b}$, $Y^{5c}$, $Y^{5d}$, $Y^{5e}$, $Y^{6a}$, $Y^{6b}$, $Y^{6c}$, $Y^{6d}$, and $Y^{6e}$ is a chiral center or includes one or more chiral centers.

The present disclosure further provides an organometallic complex of general formula (4),

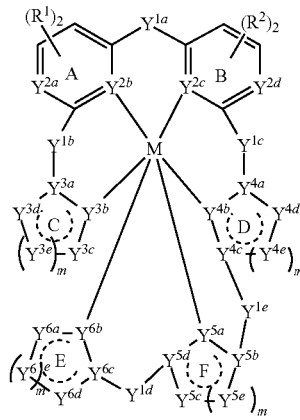

(4)

wherein:
M is a metal ion;
each $R^1$ and $R^2$ is independently selected from the group consisting of hydrogen, halogen, hydroxyl, amino, nitro, thiol, and substituted or unsubstituted $C_1$-$C_4$ alkyl;

$Y^{1a}$ is selected from the group consisting of O, S, $NR^{4a}$, $BR^{4a}$, $Si(R^{4b})_2$, and $C(R^{4c})_2$, $R^{4a}$ is substituted or unsubstituted $C_1$-$C_4$ alkyl;

each $R^{4b}$ is independently selected from substituted or unsubstituted $C_1$-$C_4$ alkyl;

each $R^{4c}$ is independently selected from hydrogen and substituted or unsubstituted $C_1$-$C_4$ alkyl;

$Y^{1c}$ is selected from the group consisting of O, S, $NR^{5a}$, $BR^{5a}$, $Si(R^{5b})_2$, and $C(R^{5c})_2$, $R^{4a}$ is substituted or unsubstituted $C_1$-$C_4$ alkyl;

each $R^{5b}$ is independently selected from substituted and unsubstituted $C_1$-$C_4$ alkyl;

each $R^{5c}$ is independently selected from hydrogen and substituted or unsubstituted $C_1$-$C_4$ alkyl;

$Y^{1d}$ is selected from the group consisting of O, S, $NR^{4a}$, $BR^{4a}$, $Si(R^{4b})_2$, and $C(R^{4c})_2$, $R^{4a}$ is substituted or unsubstituted $C_1$-$C_4$ alkyl;

each $R^{4b}$ is independently selected from substituted and unsubstituted $C_1$-$C_4$ alkyl;

each $R^{4c}$ is independently selected from hydrogen and substituted or unsubstituted $C_1$-$C_4$ alkyl;

$Y^{1d}$ is selected from the group consisting of O, S, $NR^{4a}$, $BR^{4a}$, $Si(R^{4b})_2$, and $C(R^{4c})_2$, $R^{4a}$ is substituted or unsubstituted $C_1$-$C_4$ alkyl;

each $R^{4b}$ is independently selected from substituted and unsubstituted $C_1$-$C_4$ alkyl;

each $R^{4c}$ is independently selected from hydrogen and substituted or unsubstituted $C_1$-$C_4$ alkyl;

$Y^{1e}$, when present, is selected from the group consisting of a direct bond, O, S, $NR^{4a}$, $BR^{4a}$, $Si(R^{4b})_2$, and $C(R^{4c})_2$;

$R^{4a}$ is substituted or unsubstituted $C_1$-$C_4$ alkyl;

each $R^{4b}$ is independently selected from substituted and unsubstituted $C_1$-$C_4$ alkyl;

each $R^{4c}$ is independently selected from hydrogen and substituted or unsubstituted $C_1$-$C_4$ alkyl;

each $Y^{2a}$, $Y^{2b}$, $Y^{2c}$, and $Y^{2d}$ is independently selected from the group consisting of O, S, N, $NR^{6a}$, $BR^{6a}$, and $CR^{6b}$;

each $R^{6a}$ and $R^{6b}$ is independently selected from the group consisting of hydrogen, halogen, hydroxyl, amino, nitro, thiol, and substituted or unsubstituted $C_1$-$C_4$ alkyl;

each $Y^{3a}$, $Y^{3b}$, $Y^{3c}$, $Y^{3d}$, $Y^{3e}$, $Y^{4a}$, $Y^{4b}$, $Y^{4c}$, $Y^{4d}$, and $Y^{4e}$ is independently selected from the group consisting of N, O, S, $NR^{6a}$, $BR^{6a}$, $CR^{6b}$, and $Z(R^{6c})_2$;

Z is C or Si;

each $R^{6a}$ and $R^{6b}$ is independently selected from hydrogen and substituted or unsubstituted $C_1$-$C_4$ alkyl;

each $R^{6c}$ is independently selected from hydrogen and substituted or unsubstituted $C_1$-$C_4$ alkyl;

each m is independently 1 or 2;

$\overset{(\phantom{x})}{\underset{\phantom{x}\_\phantom{x}}{}}$ represents partial or full unsaturation of the ring with which it is associated;

each $Y^{5a}$, $Y^{5b}$, $Y^{5c}$, $Y^{5d}$, $Y^{5e}$, $Y^{6a}$, $Y^{6b}$, $Y^{6c}$, $Y^{6d}$, and $Y^{6e}$ is independently selected from the group consisting of N, O, S, $NR^{6a}$, and $CR^{6b}$;

each ring A, B, C, D, E, and F is independently optionally fused to one or two independently selected $C_{3-6}$ cycloalkyl, $C_{6-10}$ aryl, or 4-10 membered heterocycloalkyl groups; and at least one of M, $R^1$, $R^2$, $Y^{1a}$, $Y^{1b}$, $Y^{1c}$, $Y^{1d}$, $Y^{1e}$, $Y^{2a}$, $Y^{2b}$, $Y^{2c}$, $Y^{2d}$, $Y^{3a}$, $Y^{3b}$, $Y^{3c}$, $Y^{3d}$, $Y^{3e}$, $Y^{4a}$, $Y^{4b}$, $Y^{4c}$, $Y^{4d}$, $Y^{4e}$, $Y^{5a}$, $Y^{5b}$, $Y^{5c}$, $Y^{5d}$, $Y^{5e}$, $Y^{6a}$, $Y^{6b}$, $Y^{6c}$, $Y^{6d}$, and $Y^{6e}$ is a chiral center or includes one or more chiral centers.

In some aspects of general formulae (1)-(4), M is selected from the group consisting of $Pt^{2+}$, $Pd^{2+}$, $Ir^+$, $Rh^+$, $Au^{3+}$, $Ir^{3+}$, $Rh^{3-}$, $Ru^{2+}$, $Pt^{4'}$, and $Os^{2+}$. In some aspects of general formulae (1)-(4), M is selected from the group consisting of $Pt^{2+}$, $Pt^{4+}$, $Ir^+$, and $Ir^{3+}$. In some aspects of general formulae (1)-(4), M is $Pt^{2+}$ or $Pt^{4+}$. In some aspects of general formulae (1)-(4), M is $Ir^+$ or $Ir^+$. In some aspects of general formulae (1)-(4), M is a chiral center.

In some aspects of general formula (1), each $Y^{1a}$ and $Y^{1b}$, when present, is independently selected from the group consisting of a direct bond, NH, and $CH_2$. In some aspects of general formula (1), each $Y^{2a}$, $Y^{2b}$, $Y^{2c}$, $Y^{2d}$, $Y^{3a}$, $Y^{3b}$, $Y^{3c}$, $Y^{3d}$, $Y^{3e}$, $Y^{4a}$, $Y^{4b}$, $Y^{4c}$, $Y^{4d}$ and $Y^{4e}$ is independently selected from C, CH, N, and NH.

In some aspects of general formula (2), each $Y^{1a}$, $Y^{1b}$, and $Y^{1c}$, when present, is independently selected from the group consisting of a direct bond, NH, and $CH_2$. In some aspects of general formula (2) each $Y^{2a}$, $Y^{2b}$, $Y^{2c}$, $Y^{2d}$, $Y^{3a}$, $Y^{3b}$, $Y^{3c}$, $Y^{3d}$, $Y^{3e}$, $Y^{4a}$, $Y^{4b}$, $Y^{4c}$, $Y^{4d}$, and $Y^{4e}$ is independently selected from C, CH, N, and NH.

In some aspects of general formula (3), each $Y^{2a}$, $Y^{2b}$, $Y^{2c}$, $Y^{2d}$, $Y^{3a}$, $Y^{3b}$, $Y^{3c}$, $Y^{3d}$, $Y^{3e}$, $Y^{4a}$, $Y^{4b}$, $Y^{4c}$, $Y^{4d}$, $Y^{4e}$, $Y^{5a}$, $Y^{5b}$, $Y^{5c}$, $Y^{5d}$, $Y^{5e}$, $Y^{6a}$, $Y^{6b}$, $Y^{6c}$, $Y^{6d}$, and $Y^{6e}$ is independently selected from C, CH, N, and NH.

In some aspects of general formula (4), each $Y^{1a}$, $Y^{1b}$, $Y^{1c}$, $Y^{1d}$, and $Y^{1e}$, when present, is independently selected from the group consisting of a direct bond, NH, and $CH_2$. In some aspects of general formula (4), each $Y^{2a}$, $Y^{2b}$, $Y^{2c}$, $Y^{2d}$, $Y^{3a}$, $Y^{3b}$, $Y^{3c}$, $Y^{3d}$, $Y^{3e}$, $Y^{4a}$, $Y^{4b}$, $Y^{4c}$, $Y^{4d}$, $Y^{4e}$, $Y^{5a}$, $Y^{5b}$, $Y^{5c}$, $Y^{5d}$, $Y^{5e}$, $Y^{6a}$, $Y^{6b}$, $Y^{6c}$, $Y^{6d}$, and $Y^{6e}$ is independently selected from C, CH, N, and NH.

In some aspects of general formulae (1)-(4), $\overset{(\phantom{x})}{\underset{\phantom{x}\_\phantom{x}}{}}$ represents full unsaturation of the ring with which it is associated or partial unsaturation of the ring with which it is associated.

In some aspects of general formulae (1)-(2), each ring A, B, C, and D is independently selected from optionally substituted phenyl, optionally substituted pyridinyl, optionally substituted pyrazolyl, and optionally substituted imidizolyl. In some aspects of general formulae (1)-(2), each ring A, B, C, and D is independently selected from phenyl, difluorophenyl, pyridinyl, pyrazolyl, dimethylpyrazolyl, and methylimidzolyl. In some aspects of general formulae (1)-(2), at least one of rings A, B, C, and D is optionally fused to one or two $C_{3-6}$ cycloalkyl, $C_{6-10}$ aryl or 4-10 member heterocycloalkyl groups. In some aspects of general formulae (1)-(2), at least one of rings A, B, C, and D is optionally fused to one $C_{3-6}$ cycloalkyl group or one 4-10 member heterocycloalkyl group.

In some aspects of general formulae (3)-(4), each ring A, B, C, D, E, and F is independently selected from optionally substituted phenyl, optionally substituted pyridinyl, and optionally substituted pyrazolyl. In some aspects of general formulae (3)-(4), each ring A, B, C, D, E, and F is independently selected from phenyl, difluorophenyl, pyridinyl, and dimethylpyrazolyl. In some aspects of general formulae (3)-(4), at least one of rings A, B, C, D, E, and F is optionally fused to one or two $C_{3-6}$ cycloalkyl, $C_{6-10}$ aryl or 4-10 member heterocycloalkyl groups. In some aspects of general formulae (3)-(4), at least one of rings A, B, C, D, E, and F is optionally fused to one $C_{3-6}$ cycloalkyl group or one $C_{6-10}$ aryl group.

In some aspects, the chiral metal complex disclosed herein is selected from the group consisting of:

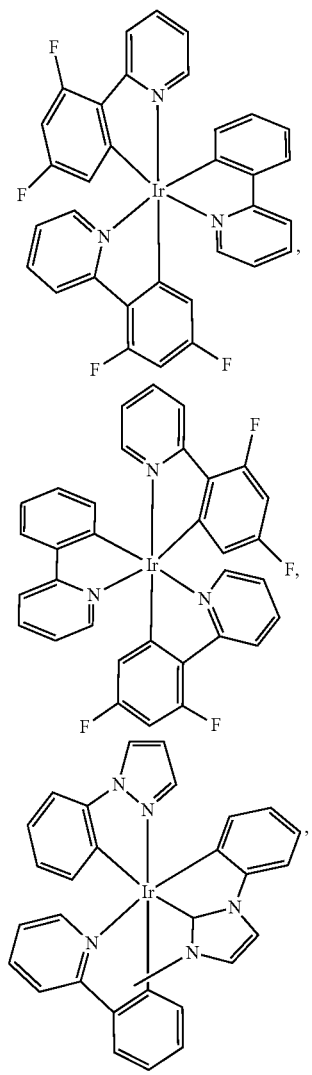

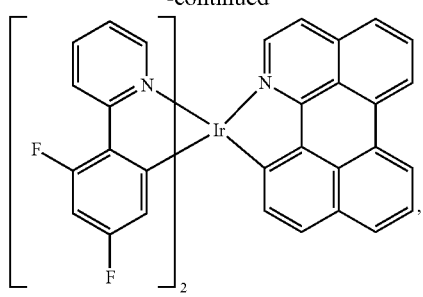
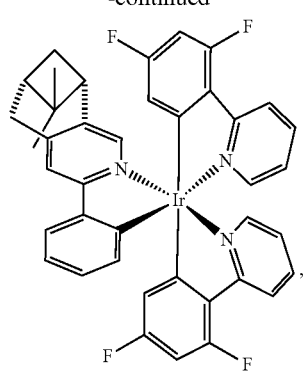
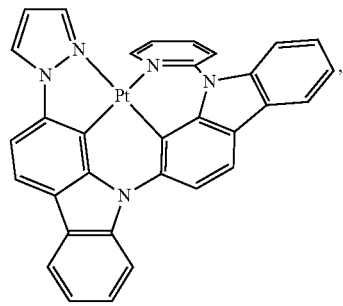
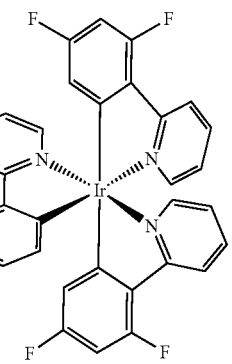
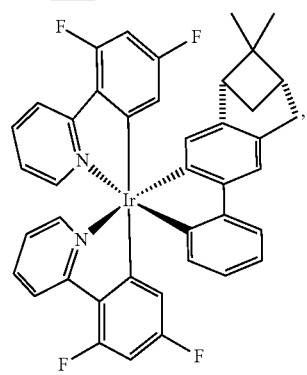
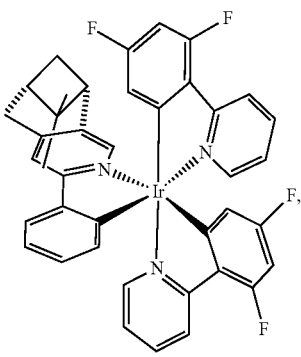
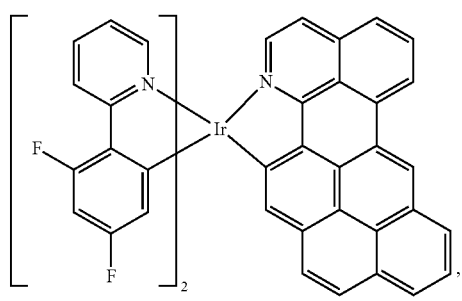
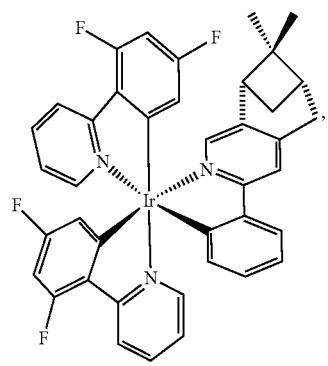
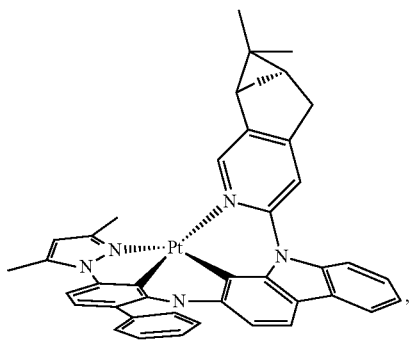

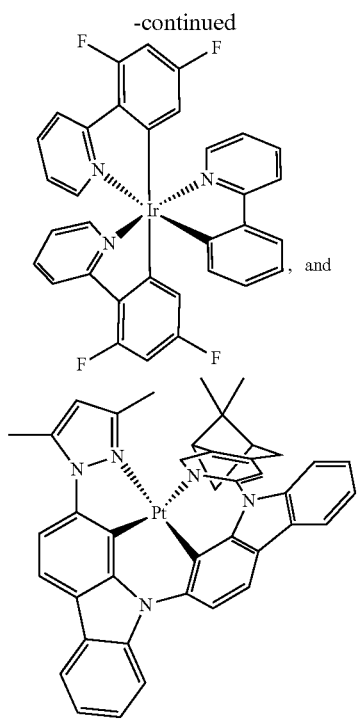

Light Emitting Devices

The compounds disclosed herein are useful in a variety of applications. As light emitting materials, the compounds can be useful in organic light emitting diodes (OLEDs), luminescent devices and displays, and other light emitting devices.

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

Chiral emitters described herein generate circularly polarized electroluminescent emission. OLEDs that comprise said chiral emitters in the emissive materials layer (EML) provide circularly polarized electroluminescence without the use of polarizers and the accompanying loss of efficiency.

Circularly polarized emission is generated when greater than 50 wt % or mol % of the emissive material in the emissive materials layer (EML) is a selected single enantiomer or a selected single diastereomer of the chiral metal complex emitters of general formulae (1)-(4). In some aspects, greater than 60, 70, 80, 90, 95, or 99 wt % or mol % of the emissive material in the emissive materials layer is a selected single enantiomer or a selected single diastereomer of the chiral metal complex emitters of general formulae (1)-(4). In some aspects, greater than 60, 70, 80, 90, 95, or 99 wt % of the emissive material in the emissive materials layer is a selected single enantiomer or a selected single diastereomer of the chiral metal complex emitters of general formulae (1)-(4). In some aspects, greater than 60, 70, 80, 90, 95, or 99 mol % of the emissive material in the emissive materials layer is a selected single enantiomer or a selected single diastereomer of the chiral metal complex emitters of general formulae (1)-(4). The chiral metal complex emitters in the emissive materials layer may be present as a single chiral structure, an isomeric mixture, or two or more different chiral metal complexes. In some aspects, the chiral metal complex emitter in the emissive materials layer is present as a single chiral structure. In some aspects, the chiral metal complex emitter in the emissive materials layer is present as an isomeric mixture. In some aspects, two or more different chiral metal complexes are present in the emissive materials layer.

NMR spectra were recorded on a Varian Gemini-300, Varian Gemini-400 and other instrument and chemical shifts were referenced to residual protiated solvent. HPLC was performed on HPLC Agilent Technologies 1200 Series equipped with CHIRALPAK ID-3 and other chiral columns. Circular dichroism (CD) spectra were recorded on a JASCO J-710 CD spectropolarimeter.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and not intended to limit the scope of the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Various methods for the preparation method of the compounds described herein are recited in the examples. These methods are provided to illustrate various methods of preparation, but this disclosure is not intended to be limited to any of the methods recited herein. Accordingly, one of skill in the art in possession of this disclosure could readily modify a recited method or utilize a different method to prepare one or more of the compounds. The following aspects are only exemplary and are not intended to limit the scope of the disclosure. Temperatures, catalysts, concentrations, reactant compositions, and other process conditions can vary, and one of skill in the art, in possession of this disclosure, could readily select appropriate reactants and conditions for a desired complex.

Example 1

Figure 6:
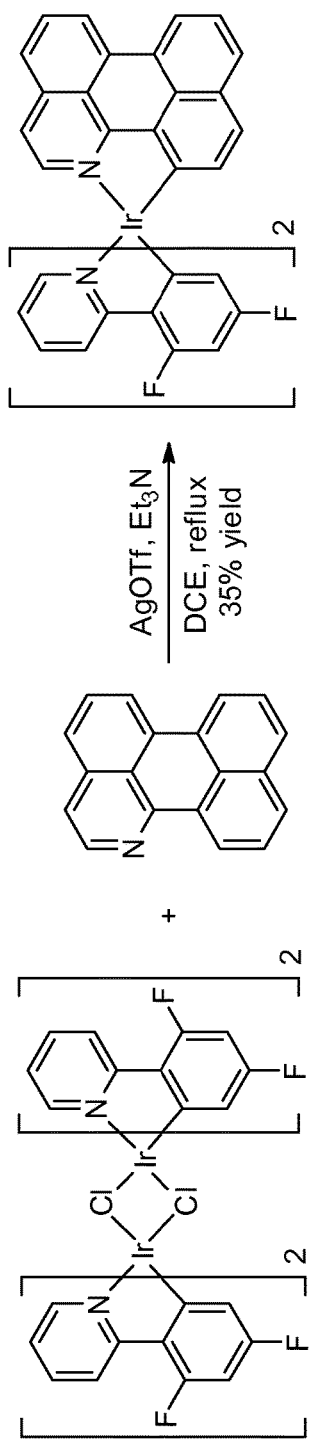
FIG. 6 depicts synthesis of a chiral metal complex.

The chiral metal complex shown in structural formula (A) was synthesized as shown in FIG. 6, according to the process described below:

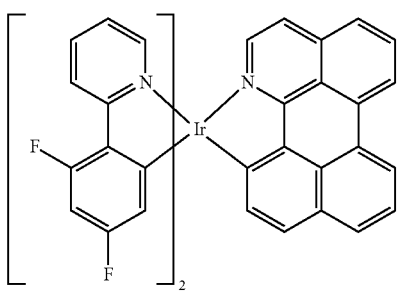

(A)

A mixture of chloride-bridged Ir(III) dimer [(dfppy)$_2$Ir(μ-Cl)]$_2$ (0.3 g), azaperylene ligand (0.15 g), silver triflate (0.3 g), and 2-3 eq. of triethylamine was stirred in a solution of 50 mL dichloroethane for 2 h at room temperature. The reaction mixture was heated at reflux for an additional 12 h. Then the mixture was cooled to room temperature, and the precipitate was filtered off. The filtrate was evaporated to dryness under reduced pressure, and the dark red crystalline product (yield: 35%) was obtained from column chromatography on silica using a CH$_2$Cl$_2$ mobile phase. The final product can be further purified in a thermal gradient sublimation method. $^1$H NMR (300 MHz, CDCl$_3$), 8.31 (d, J=7.8 Hz, 1 H), 8.27-8.15 (m, 3 H), 7.97 (d, J=5.3 Hz 1 H), 7.75-7.64 (m, 3 H), 7.59-7.41 (m, 6 H), 7.28 (d, J=8.4 Hz,1 H), 7.14 (d, J=5.7 Hz,1 H), 6.69 (dd, J=6.0 Hz, 6.6 Hz, 1 H), 6.65 (dd, J=6.6 Hz, 6.6 Hz, 1 H), 6.52-6.41 (m, 2 H), 6.06 (dd, J=7.5 Hz, J =2.4 Hz, 1 H), 5.93 (dd, J=8.4 Hz, J=2.4 Hz, 1 H). Anal. for C$_{41}$H$_{22}$F$_4$IrN$_3$, found: C 59.83, H 2.36, N 5.11; calcd: C 59.70, H 2.69, N 5.09.

Example 2

Figure 7:
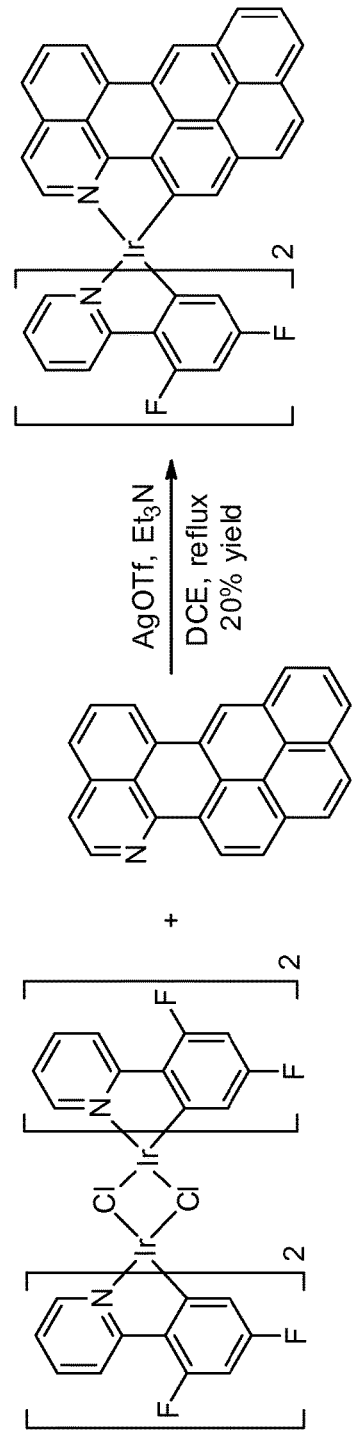
FIG. 7 depicts synthesis of a chiral metal complex.

The chiral metal complex shown in structural formula (B) was synthesized as shown in FIG. 7 according to the process described below:

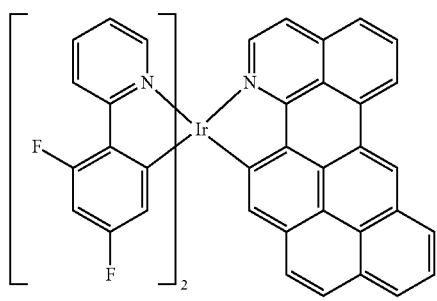

(B)

A mixture of chloride-bridged Ir(III) dimer [(dfppy)$_2$Ir(μ-Cl)]$_2$ (0.3 g), benzo[de]pyreno[10,1-gh]quinolone (0.19 g), silver triflate (0.3 g), and 2-3 eq. of triethylamine was stirred in a solution of 50 mL dichloroethane for 2 h at room temperature. The reaction mixture was heated at reflux for an additional 12 h. Then the mixture was cooled to room temperature, and the precipitate was filtered off. The filtrate was evaporated to dryness under reduced pressure, and the dark red crystalline product (yield: 20%) was obtained from column chromatography on silica using a CH$_2$Cl$_2$ mobile phase. In some aspects, the final product was further purified using a thermal gradient sublimation method. $^1$H NMR (400 MHz, CDCl$_3$, δ) 9.30 (s, 1 H), 8.92 (d, J=7.9 Hz, 1 H), 8.37 (d, J=7.4 Hz, 1 H), 8.26-8.16 (m, 3 H), 8.08-7.77 (m, 8 H), 7.74 (t, J=8.1 Hz 1 H), 7.65 (s, 1 H), 7.56 (d, J=6.4 Hz, 1 H), 7.54 (d, J=6.4 Hz, 1 H), 7.01 (t, J=6.4 Hz,1 H), 6.91 (t, J=6.6 Hz, 1 H), 6.88-6.78 (m, 2 H), 5.98 (dd, J=7.1, 2.4 Hz, 1 H), 5.87 (dd, J=8.8, 1.9 Hz, 1 H).

Example 3

Figure 8:
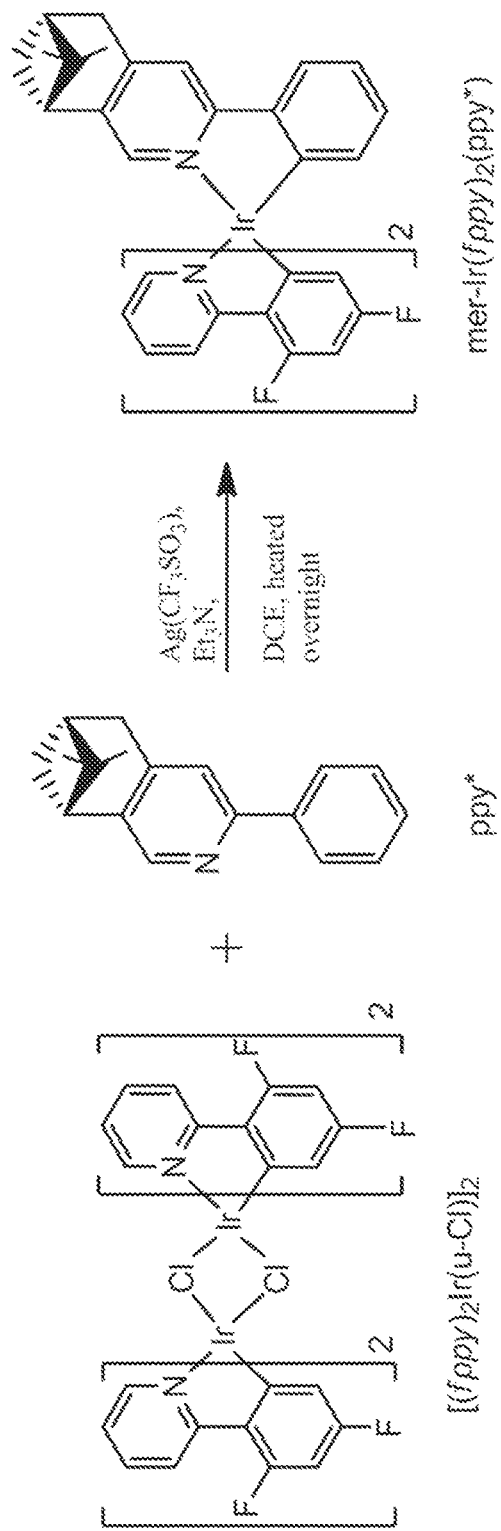
FIG. 8 depicts synthesis of a chiral metal complex.
Figure 9A:
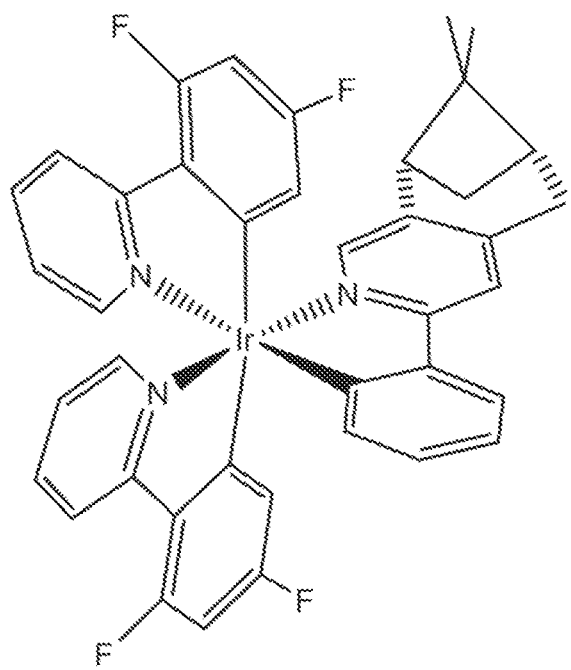
FIGS. 9A and 9B depict chiral isomers of an octahedral metal complex.
Figure 9B:
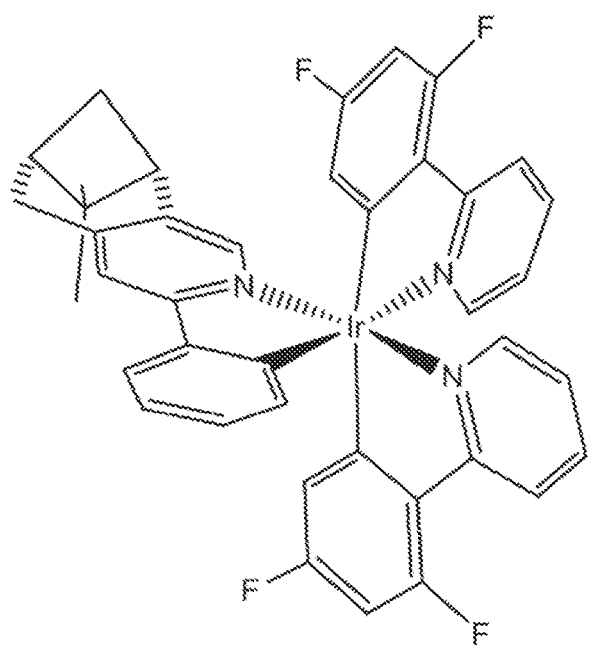

The chiral metal complex mer-Ir(fppy)$_2$(ppy*) was synthesized as shown in FIG. 8, according to the process described below:

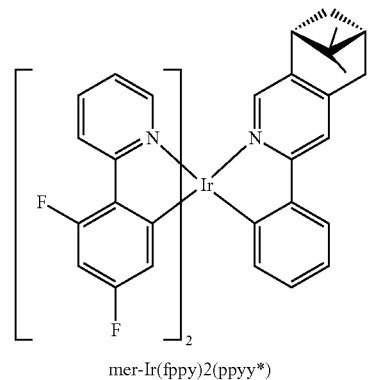

mer-Ir(fppy)2(ppyy*)

Figure 10:
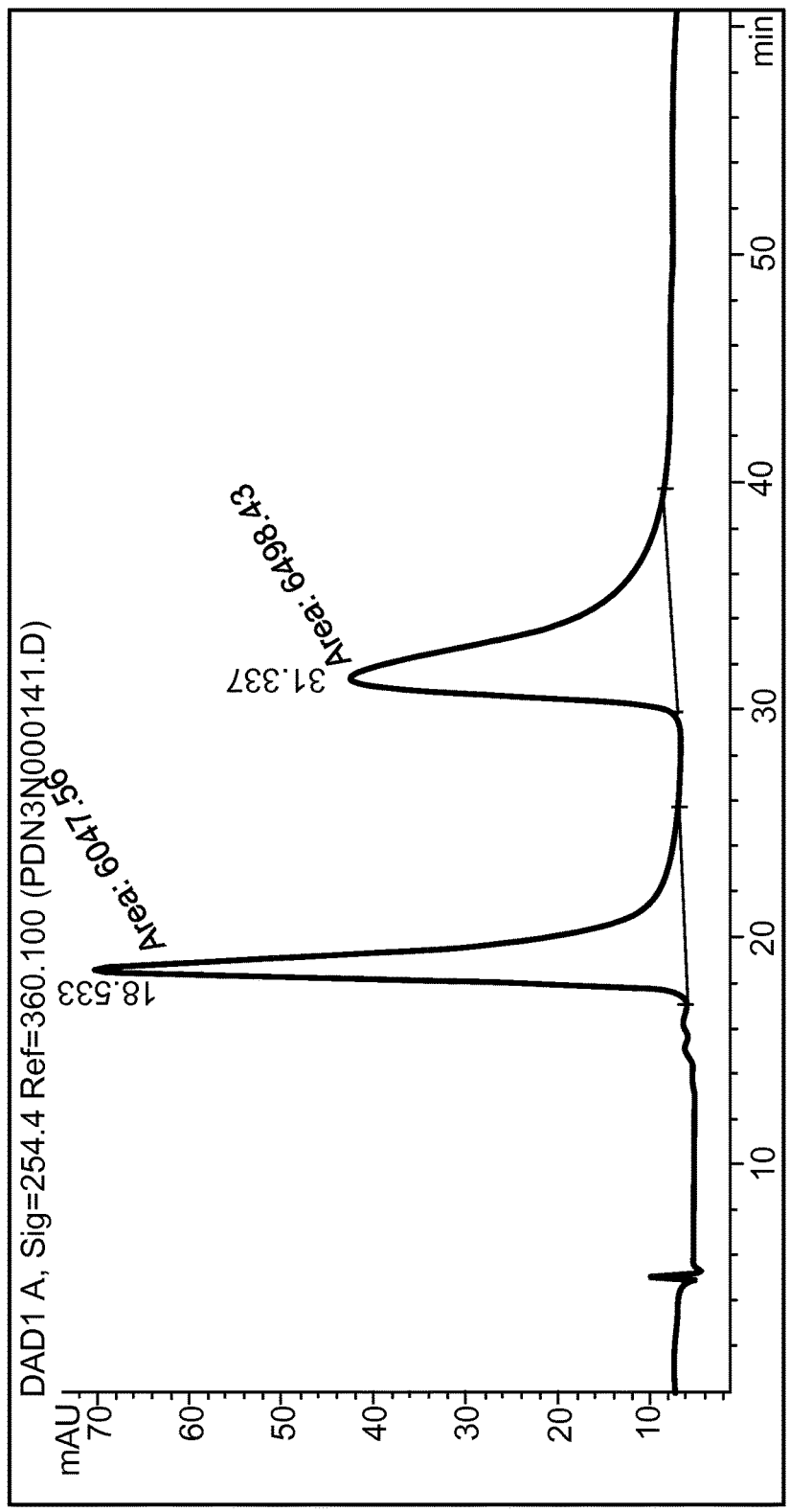
FIG. 10 shows a chiral HPLC analysis representative of a mixture of mer-Ir(fppy)$_2$(ppy*).
Figure 11A:
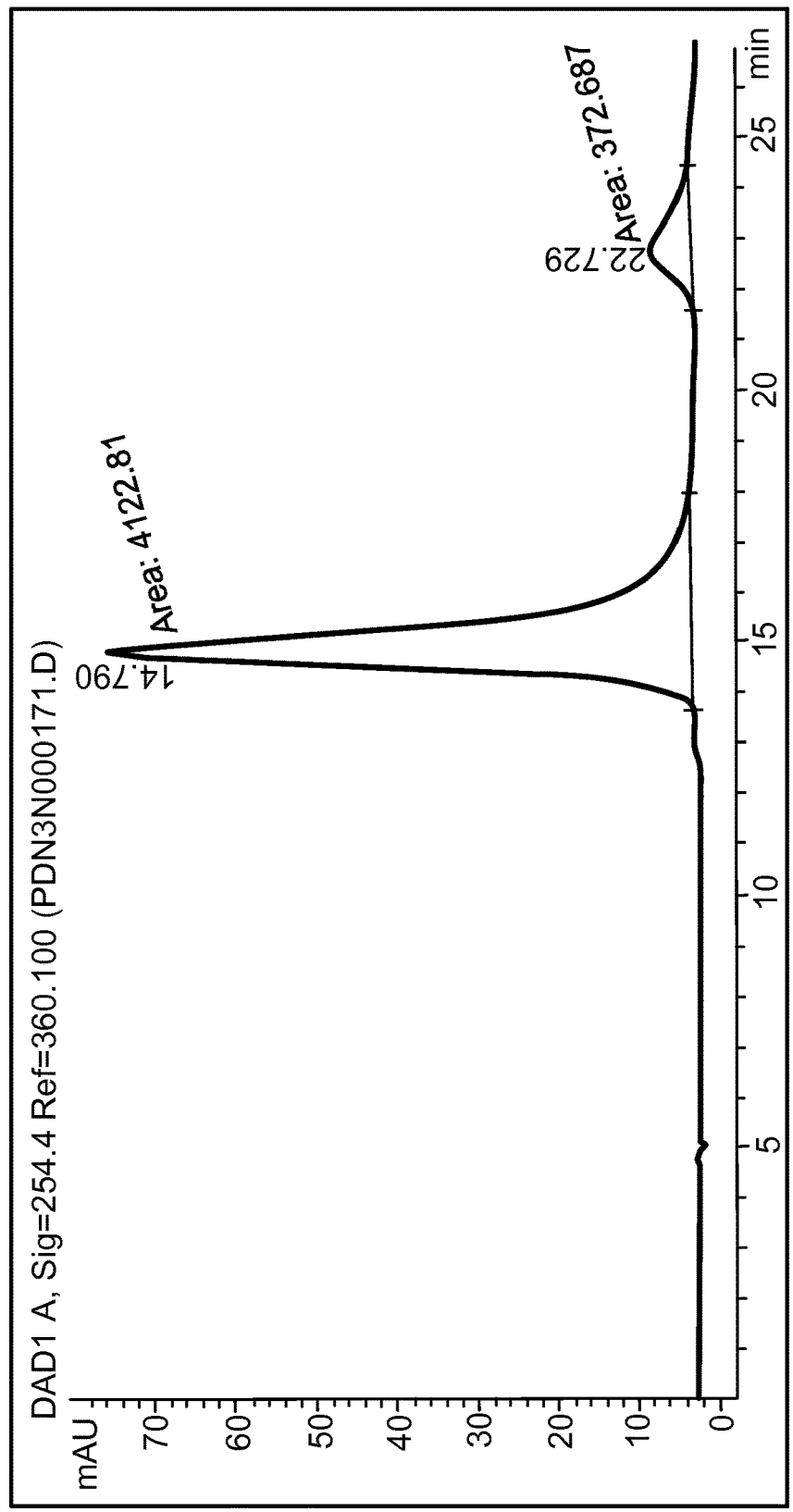
FIGS. 11A and 11B show chiral HPLC analyses representative of the chiral isomers of mer-Ir(fppy)$_2$(ppy*).
Figure 11B:
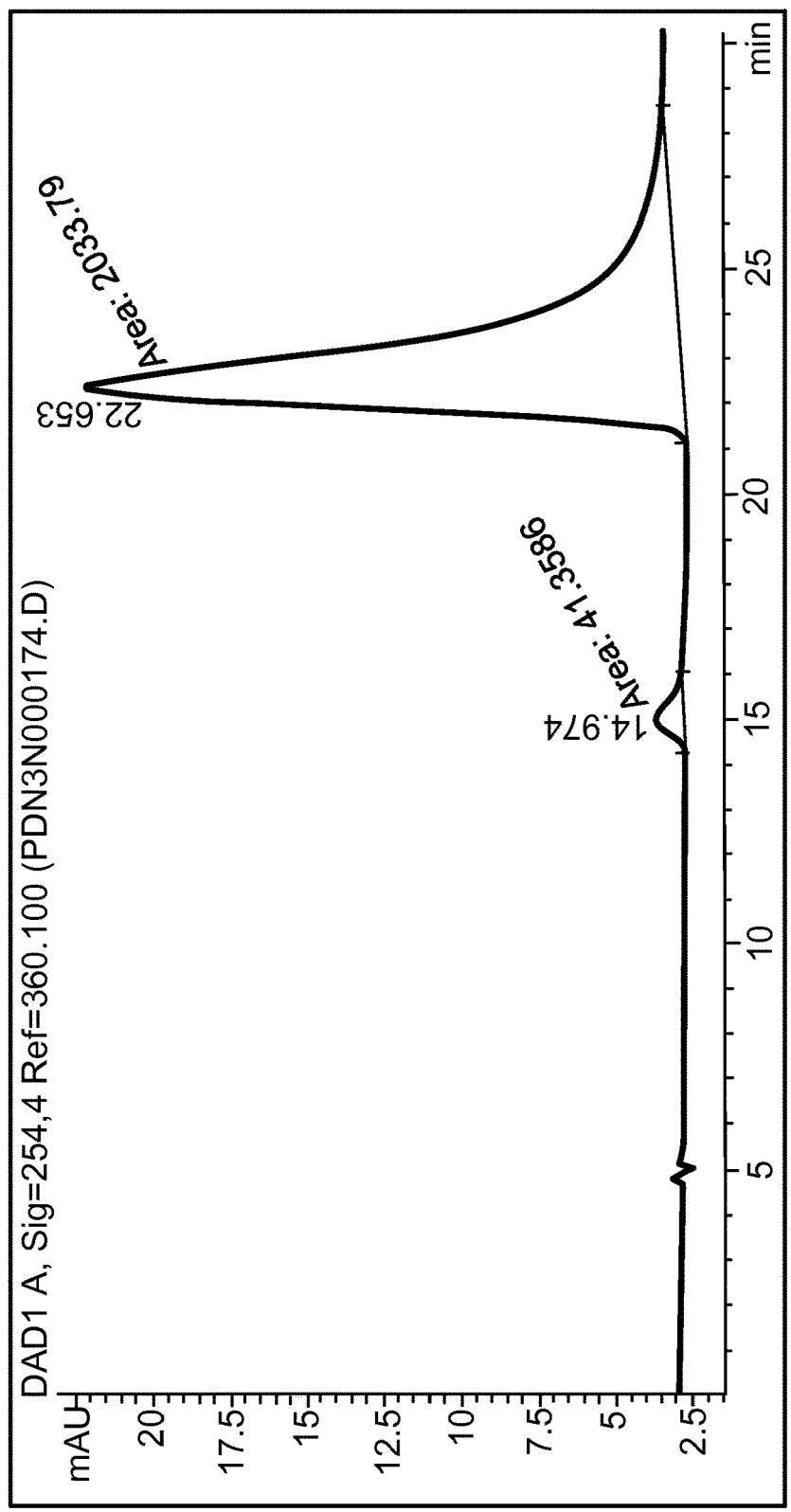
Figure 12:
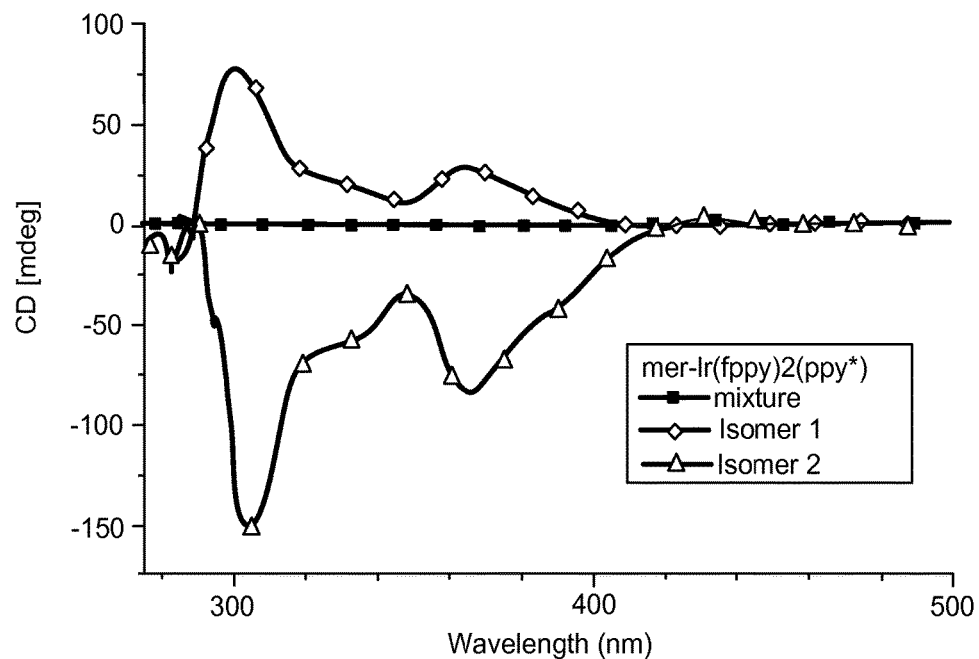
FIG. 12 shows circular dichroism (CD) spectra representative of a mixture and individual isomers of mer-Ir(fppy)$_2$(ppy*) in a solution of dichloromethane at room temperature.

A mixture of 0.3 g chloride-bridged Ir(III) dimer, [(fppy)$_2$Ir(μ-Cl)]$_2$, about 0.1 g ppy* ligand, 0.3 g silver triflate, and 2-3 eq. triethylamine was stirred in a solution of 50 mL dichloroethane for 2 h at room temperature. The reaction mixture was heated at reflux for an additional 12 h. Then the mixture was cooled to room temperature and the precipitate was filtered off The filtrate was evaporated to dryness under reduced pressure and the raw product of mer-Ir(fppy)$_2$(ppy*) was obtained from column chromatography on silica using a CH$_2$Cl$_2$ mobile phase. $^1$H NMR for mer-Ir(fppy)$_2$(ppy*) (2 isomers in approx. 1:1 ratio, not assigned). 400 MHz, DMSO-d$_6$: δ 8.25-8.11 (m, 2 H), 8.10-7.97 (m, 2 H), 7.91-7.72 (m, 3 H), 7.66 (d, J=6.2 Hz, 0.5 H), 7.48 (d, J=5.5 Hz, 0.5 H), 7.30 (s, 0.5 H), 7.26 (s, 0.5 H), 7.14-7.01 (m, 2 H), 6.99-6.83 (m, 2 H), 6.79-6.58 (m, 3 H), 5.89-5.82 (m, 1 H), 5.71-5.61 (m, 1 H), 3.20-2.96 (m, 2 H), 2.70-2.38 (m, 2 H, overlapped with solvent residual peak), 2.29-2.15 (m, 1 H), 1.33 (s, 1.5 H), 1.27 (s, 1.5 H), 1.22 (d, J=9.8 Hz, 0.5 H), 1.00 (d, J=9.3 Hz, 0.5 H), 0.68 (s, 1.5 H), 0.31 (s, 1.5 H). By running the bulk samples through HPLC equipped with selected chiral column (e.g. CHIRALPAK ID-3) for multiple times, both isomers of mer-Ir(fppy)$_2$(ppy*), as shown in FIG. 9, were separated from the mixture. HPLC traces and circular dichroism (CD) spectra of the mixture of mer-Ir(fppy)$_2$(ppy*) and the isolated isomers are shown in FIGS. 10-12.

Example 4

Figure 13:
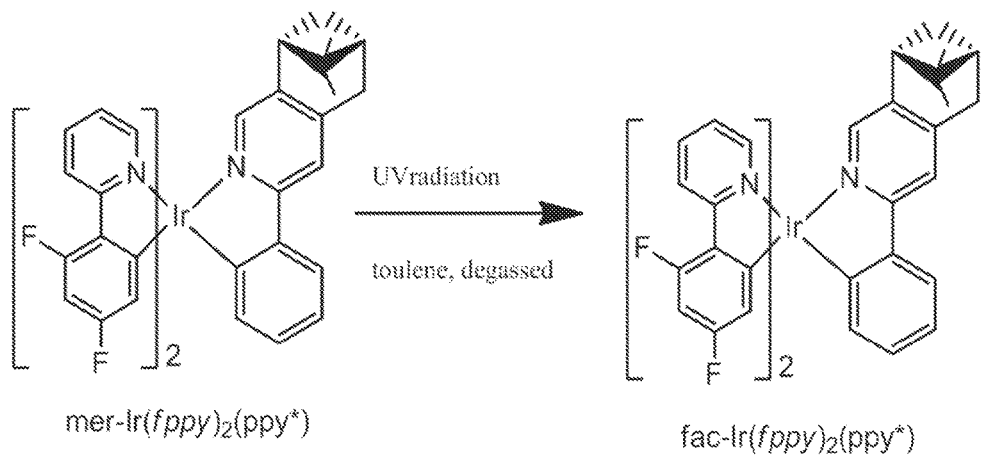
FIG. 13 depicts synthesis of a chiral metal complex.
Figure 14A:
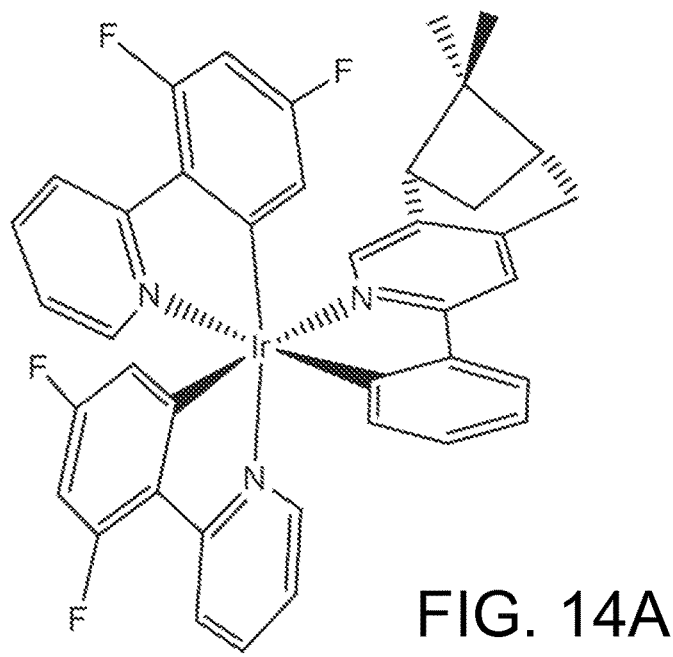
Figure 14B:
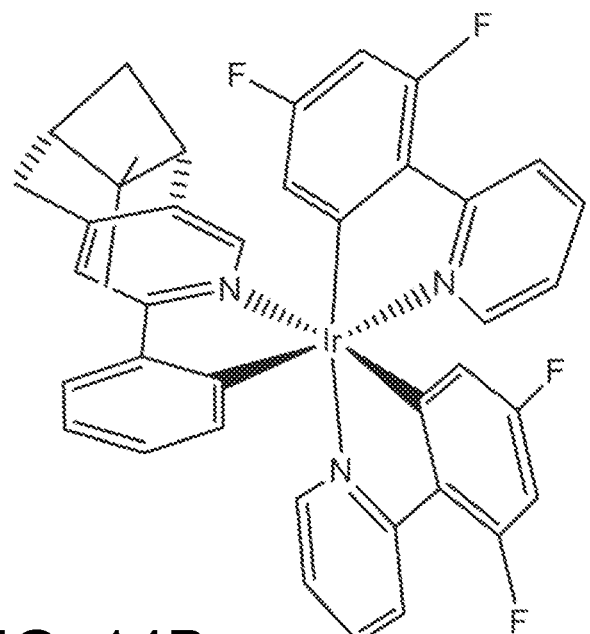

The chiral metal complexfac-Ir(fppy)$_2$(ppy*) was synthesized as shown in FIG. 13, according to the process described below:

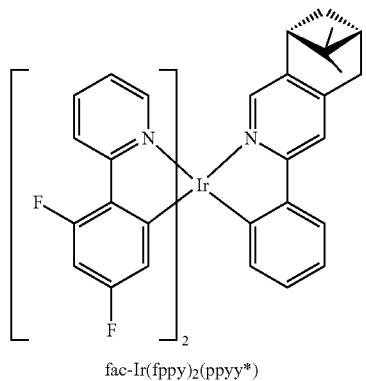

fac-Ir(fppy)₂(ppyy*)

Figure 15:
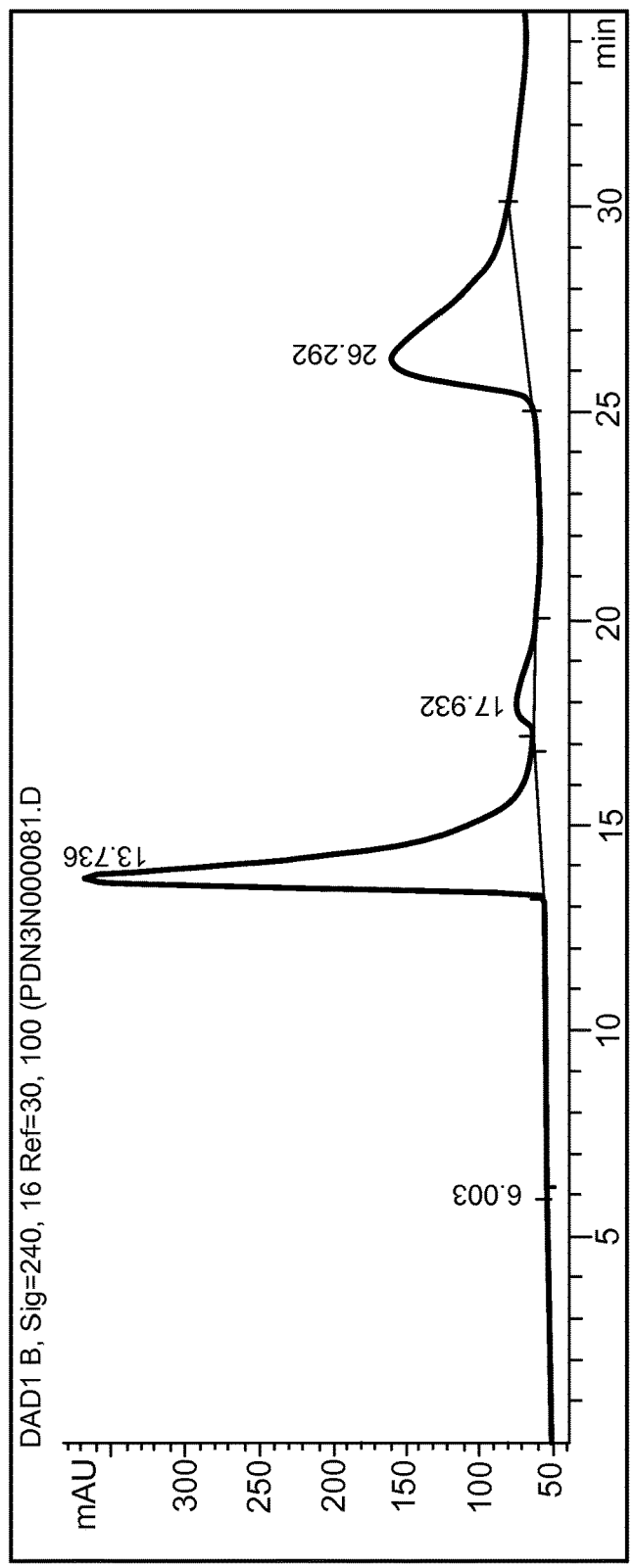
FIG. 15 shows a chiral HPLC analysis representative of the mixture of fac-Ir(fppy)$_2$(ppy*).
Figure 16:
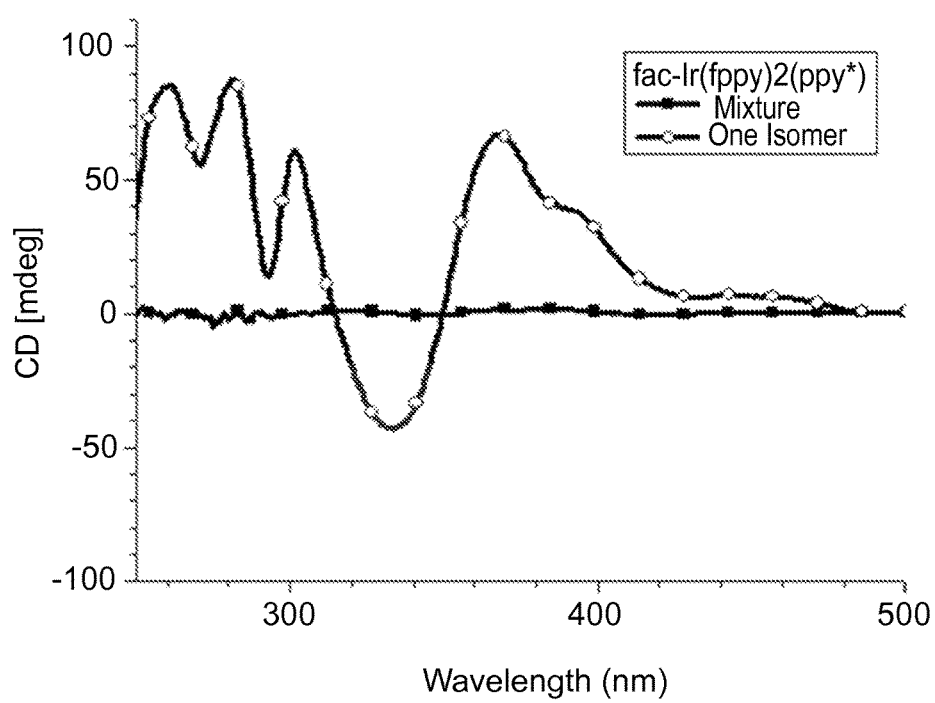
FIG. 16 shows CD spectra representative of the mixture and one isomer of fac-Ir(fppy)$_2$(ppy*) in a solution of dichloromethane at room temperature.

0.2 g of mer-Ir(fppy)₂(ppy*) was dissolved in 50 mL toluene in a sealed quartz container, which was thoroughly bubbled in a nitrogen atmosphere for 2 h. Then the mixture, under nitrogen environment, was exposed to UV radiation for 2 days. The mixture was cooled to room temperature and was evaporated to dryness under reduced pressure. The raw product offac-Ir(fppy)₂(ppy*) was obtained from column chromatography on silica using a CH₂Cl₂ mobile phase. ¹H NMR forfac-Ir(fppy)₂(ppy*) (2 isomers in approx. 1:1 ratio, not assigned). 500 MHz, DMSO-d₆: δ 8.28-8.17 (m, 2 H), 8.02 (d, J=7.3 Hz, 1 H), 7.94-7.83 (m, 2 H), 7.79-7.70 (m, 1 H), 7.56 (t, J=5.9 Hz, 1 H), 7.54-7.37 (m, 1 H), 7.28-7.10 (m, 4 H), 6.96 (d, J=12.6 Hz, 1 H), 6.90-6.81 (m, 1 H), 6.80-6.73 (m, 1 H), 6.70-6.58 (m, 2 H), 5.56-6.49 (m, 1 H), 6.15-6.10 (m, 1 H), 6.09-6.03 (m, 1 H), 3.20-2.98 (m, 2 H), 2.68-2.45 (m, 2 H, overlapped with solvent residual peak), 2.28-2.18 (m, 1 H), 1.32 (s, 1.5 H), 1.27 (s, 1.5 H), 1.22 (d, J=9.8 Hz, 0.5 H), 1.04 (d, J=9.4 Hz, 0.5 H), 0.68 (s, 1.5 H), 0.40 (s, 1.5 H). By running the bulk samples through HPLC equipped with selected chiral column (e.g. CHIRALPAK ID-3) multiple times, one isomer offac-Ir(fppy)₂(ppy*) was separated from the mixture. ¹H NMR (400 MHz, DMSO-d₆, δ): 8.35-8.18 (m, 2 H), 7.77-7.39 (m, 6 H), 6.98-6.68 (m, 6 H), 6.45-6.16 (m, 4 H), 3.18-2.96 (m, 2 H), 2.72-2.56 (m, 1 H), 2.52-2.37 (m, 1 H), 2.35-2.19 (m, 1 H), 1.35-1.19 (m, 4 H) , 0.49 (s, 3 H). The chemical structures of R— and S— isomers offac-Ir(fppy)₂(ppy*) (based on the chirality of the Iridium(III) metal ion) are shown in FIG. 14. A chiral HPLC trace of the mixture offac-Ir(fppy)₂(ppy*) is shown in FIG. 15, and a CD spectra of the mixture offac-Ir(fppy)₂(ppy*) and isolated isomer is shown in FIG. 16.

Example 5

The chiral metal complex mer-Ir(fppy)₂(ppy) was prepared as a racemic mixture (individual isomers shown below) according to the synthetic procedure for the preparation of mer-Ir(fppy)₂(ppy*), as described in Example 3.

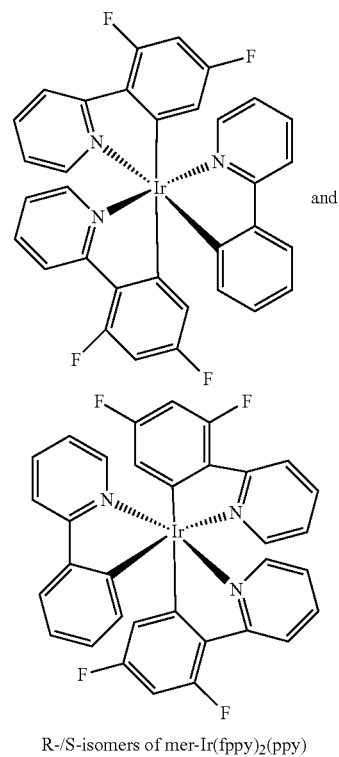

R-/S-isomers of mer-Ir(fppy)₂(ppy)

Figure 17:
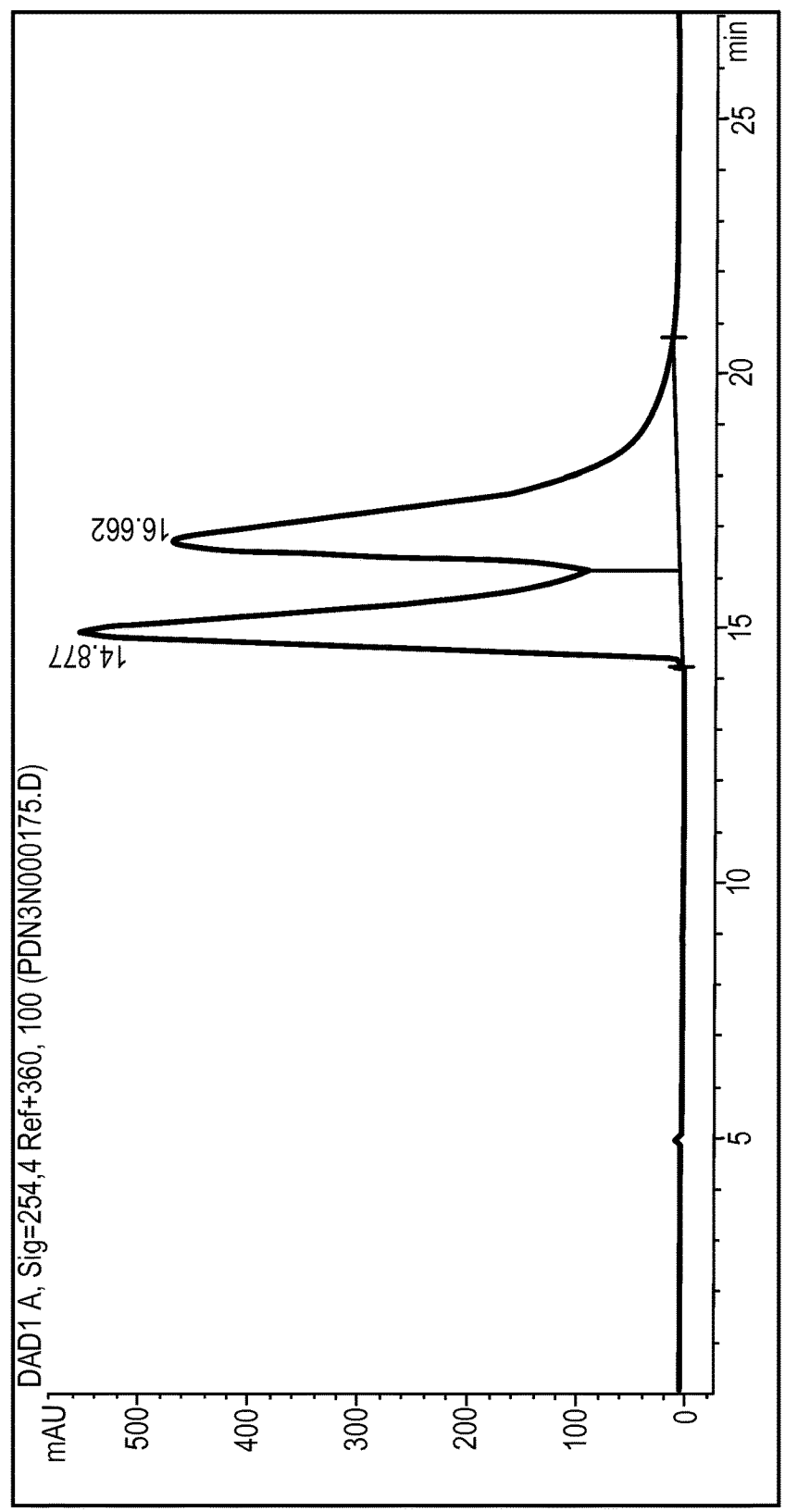
FIG. 17 shows a chiral HPLC analysis representative of racemic mer-Ir(fppy)$_2$(ppy).
Figure 18:
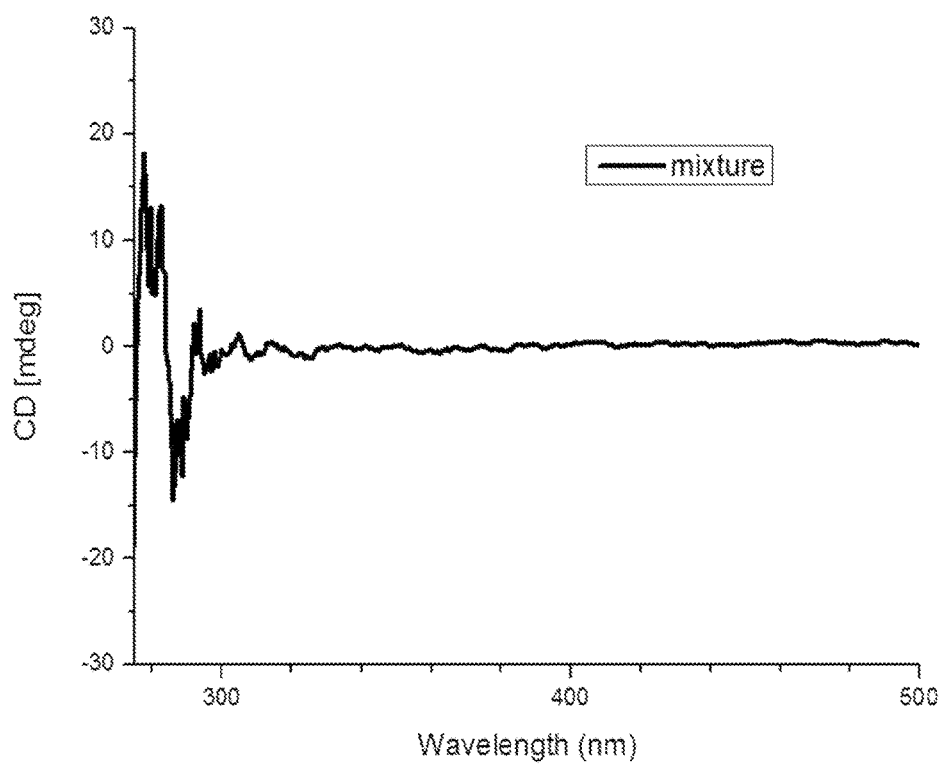
FIG. 18 shows CD spectra representative of the mixture of mer-Ir(fppy)$_2$(ppy) in a solution of dichloromethane at room temperature.

¹H NMR (400 MHz, CDCl₃, δ): 8.30-8.11 (m, 3 H), 8.03-7.97 (m, 1 H), 7.96-7.72 (m, 5 H), 7.60 (d, J=5.5 Hz, 1 H), 7.21 (t, J=6.6 Hz, 1 H), 7.13-7.04 (m, 2 H), 7.02-6.85 (m, 2 H), 6.81-6.61 (m, 3 H), 5.88 (dd, J=7.5, 2.4 Hz,1 H), 5.67 (dd, J=9.0, 2.3 Hz,1 H). A chiral HPLC trace for the racemic mixture of mer-Ir(fppy)₂(ppy) is shown in FIG. 17 and a CD spectrum of a mer-Ir(fppy)₂(ppy) is shown in FIG. 18.

Example 6

The chiral metal complex PtN1N* was prepared according to the procedure described below:

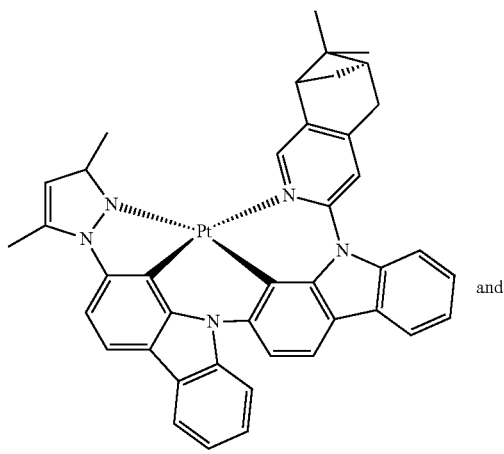

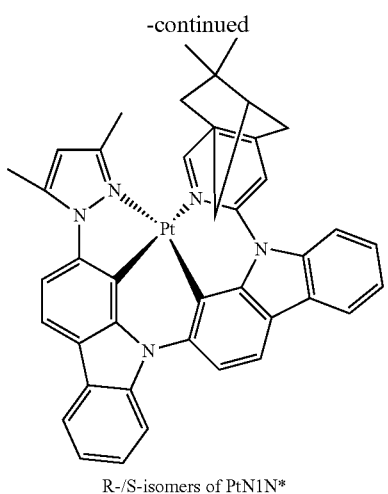

R-/S-isomers of PtN1N*

Figure 19:
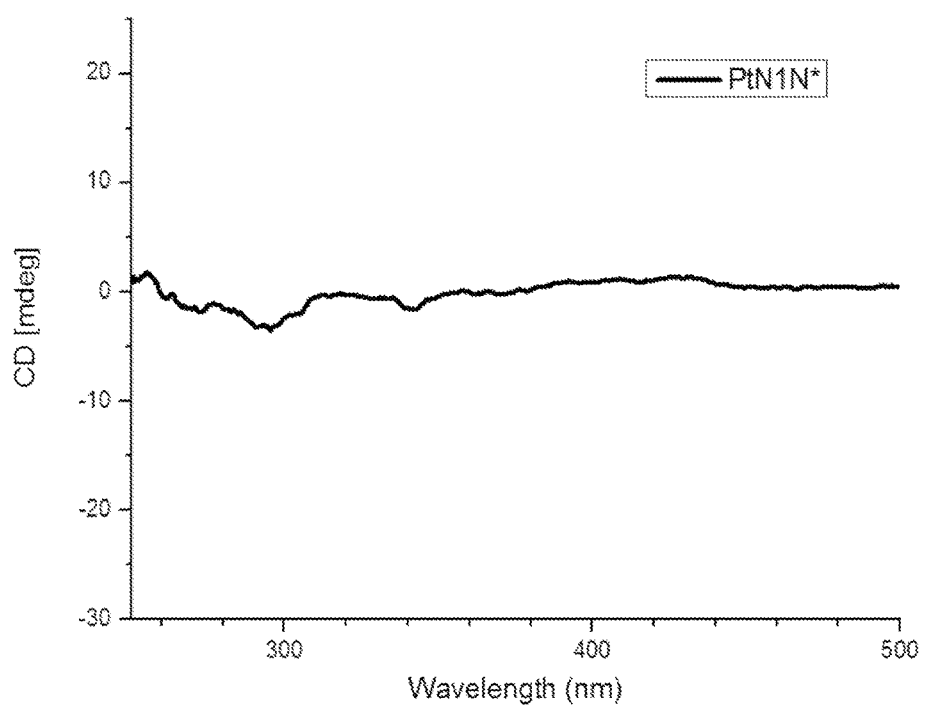
FIG. 19 shows CD spectra representative of the mixture of PtN1N* in a solution of dichloromethane at room temperature.

To a dry pressure tube equipped with a magnetic stir bar, ligand N1N* (3.0 mmol, 1.0 eq), K$_2$PtCl$_4$ (3.15 mmol, 1.05 eq), "Bu$_4$NBr (97 mg, 0.3 mmol, 0.1 eq) and acetic acid (180 mL) were added, in a nitrogen filled glove box. The mixture was bubbled with nitrogen for 30 min, sealed before being taken out of the glove box and stirred at room temperature for 20 h followed by three days at 105-115° C. The mixture was cooled to ambient temperature and water (180 mL) was added slowly. After stirring at room temperature for 10 min, the precipitate was filtered off and washed with water three times. Then the solid was dried in air under reduced pressure. The collected solid was purified via column chromatography on silica gel using dichloromethane as eluent to obtain the desired product PtN1N* as a yellow solid 872 mg in 44% yield. $^1$H NMR for PtN1N* (2 isomers in approx. 1:1 ratio, not assigned). 400 MHz, CDCl$_3$: δ 8.80 (d, J=4.3 Hz, 1 H), 8.28 (d, J=8.6 Hz, 1 H), 8.21-8.13 (m, 1 H), 8.10 (d, J=7.9 Hz,1 H), 8.07 (d, J=7.4 Hz, 1 H), 7.98-7.90 (m, 2 H), 7.90-7.80 (m, 2 H), 7.49-7.31 (m, 4 H), 7.30-7.21 (m, 1 H, overlapped with solvent residual peak), 6.08 (s, 1 H), 3.15-3.02 (m, 1 H), 2.98-2.86 (m, 1 H), 2.85-2.57 (m, 5 H), 2.46 (s, 1.5 H), 2.43 (s, 1.5 H), 2.37-2.28 (m, 1 H), 1.45 (s, 1.5 H), 1.40 (d, J=9.4 Hz, 0.5 H), 1.35 (s, 1.5 H), 1.06 (d, J=9.8 Hz, 0.5 H), 0.87 (s, 1.5 H). A CD spectrum of a mixture of PtN1N* is shown in FIG. 19.

A number of embodiments of the invention have been described. Nevertheless, it will be understood that various modifications may be made without departing from the spirit and scope of the invention. Accordingly, other embodiments are within the scope of the following claims.

What is claimed is:

1. An organometallic complex having one of the following structures:

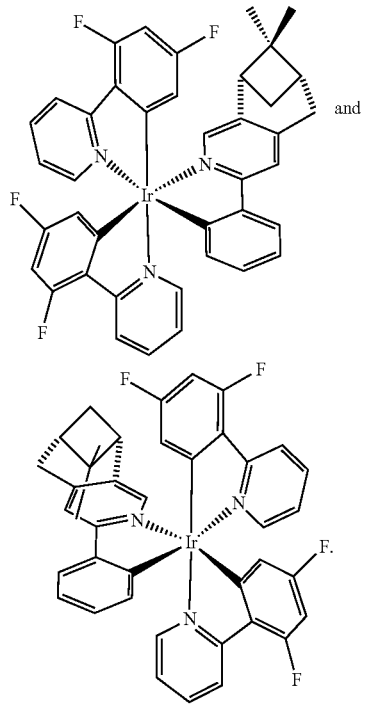

* * * * *

UNITED STATES PATENT AND TRADEMARK OFFICE
CERTIFICATE OF CORRECTION

Page 1 of 4

PATENT NO. : 10,056,567 B2
APPLICATION NO. : 15/119961
DATED : August 21, 2018
INVENTOR(S) : Jian Li It is certified that error appears in the above-identified patent and that said Letters Patent is hereby corrected as shown below:

On the Title Page

Column 2 (item (57) Abstract), delete:

"

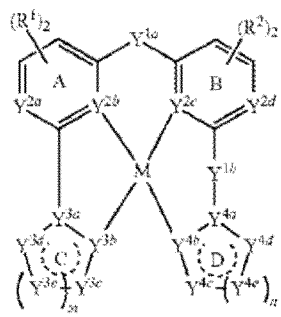

(1)

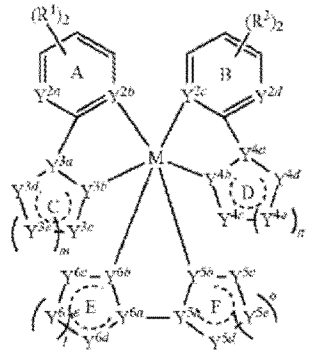

(3)

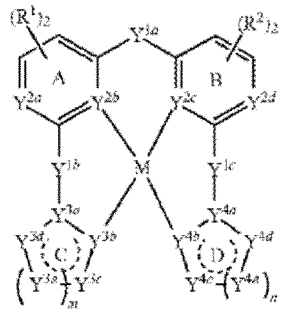

(2)

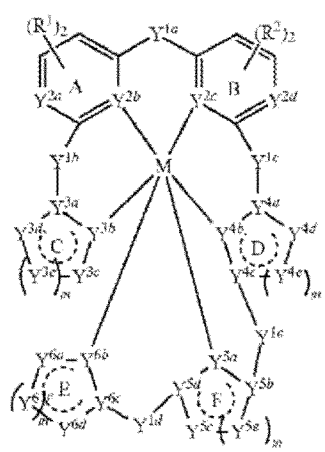

(4)

",

Signed and Sealed this
Fourteenth Day of February, 2023

Katherine Kelly Vidal
*Director of the United States Patent and Trademark Office*

And insert:
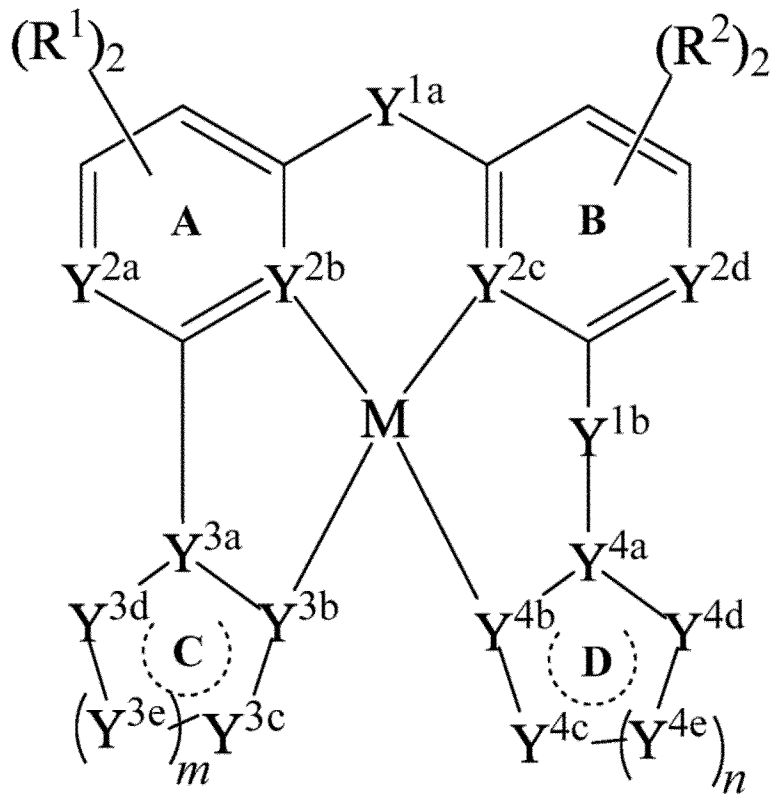
(1)
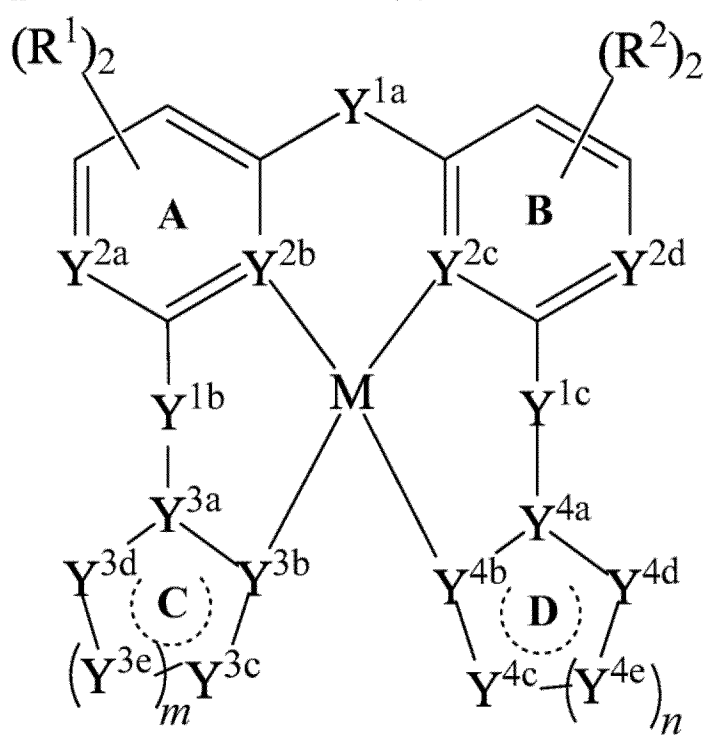
(2)

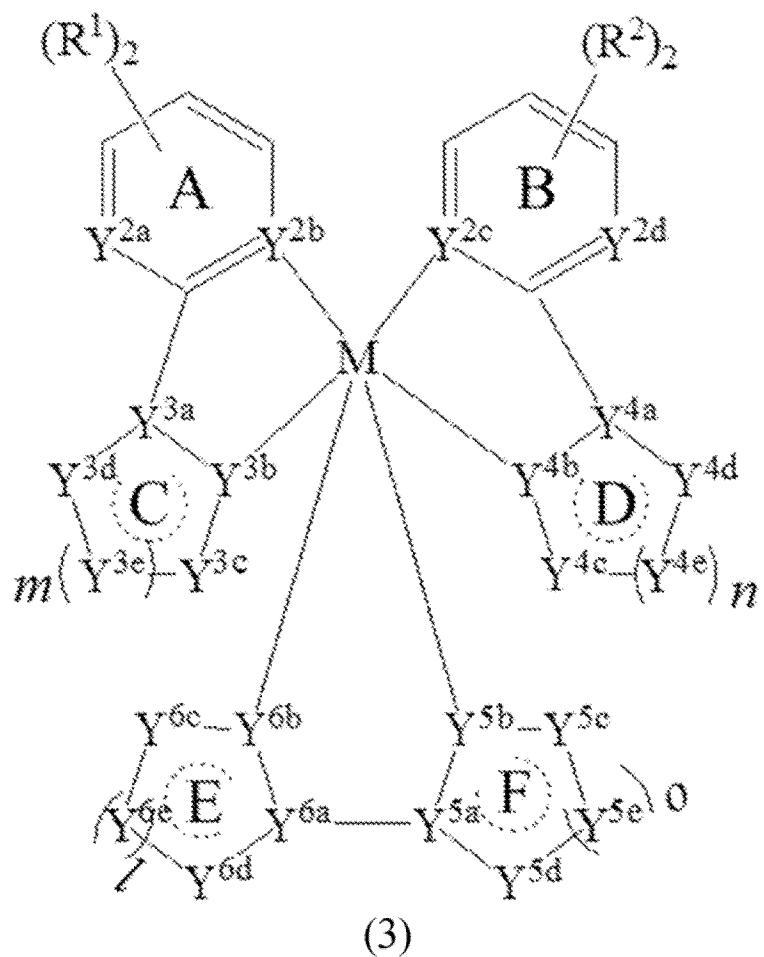
(3)

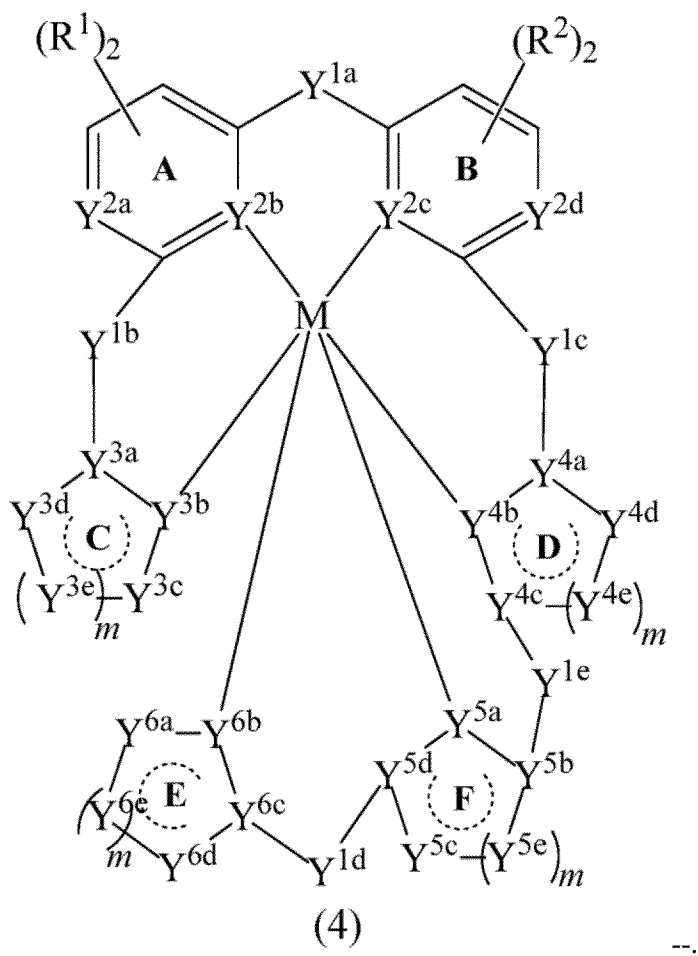
(4)